United States Patent
Welker-Nieuwoudt et al.

(10) Patent No.: US 9,181,169 B2
(45) Date of Patent: Nov. 10, 2015

(54) PROCESS FOR HETEROGENEOUSLY CATALYZED GAS PHASE PARTIAL OXIDATION OF (METH)ACROLEIN TO (METH)ACRYLIC ACID

(71) Applicant: BASF SE, Ludwigshafen (DE)

(72) Inventors: Cathrin Alexandra Welker-Nieuwoudt, Birkenheide (DE); Andrey Karpov, Metuchen, NJ (US); Frank Rosowski, Berlin (DE); Klaus Joachim Mueller-Engel, Stutensee (DE); Herbert Vogel, Nauheim (DE); Alfons Drochner, Niedernhausen (DE); Nina Blickhan, Babenhausen (DE); Nadine Duerr, Alsbach-Haehnlein (DE); Tim Jekewitz, Frankfurt (DE); Nadine Menning, Darmstadt (DE); Tina Petzold, Darmstadt (DE); Sabine Schmidt, Darmstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/888,542

(22) Filed: May 7, 2013

(65) Prior Publication Data
US 2014/0018572 A1   Jan. 16, 2014

Related U.S. Application Data

(60) Provisional application No. 61/645,082, filed on May 10, 2012.

(30) Foreign Application Priority Data

May 10, 2012   (DE) .......................... 10 2012 207 811

(51) Int. Cl.
| | |
|---|---|
| C07C 51/16 | (2006.01) |
| B01J 23/30 | (2006.01) |
| B01J 23/888 | (2006.01) |
| B01J 35/00 | (2006.01) |
| B01J 35/02 | (2006.01) |
| B01J 35/10 | (2006.01) |
| B01J 37/00 | (2006.01) |
| B01J 37/02 | (2006.01) |
| B01J 37/04 | (2006.01) |
| B01J 37/06 | (2006.01) |
| B01J 37/08 | (2006.01) |
| B01J 37/10 | (2006.01) |
| C01G 39/00 | (2006.01) |
| C01G 41/00 | (2006.01) |
| C08F 220/06 | (2006.01) |
| C07C 51/25 | (2006.01) |
| B01J 37/03 | (2006.01) |

(Continued)

(52) U.S. Cl.
CPC ............... *C07C 51/16* (2013.01); *B01J 23/002* (2013.01); *B01J 23/30* (2013.01); *B01J 23/8885* (2013.01); *B01J 35/002* (2013.01); *B01J 35/023* (2013.01); *B01J 35/1014* (2013.01); *B01J 37/0009* (2013.01); *B01J 37/0036* (2013.01); *B01J 37/0045* (2013.01); *B01J 37/0221* (2013.01); *B01J 37/0223* (2013.01); *B01J 37/033* (2013.01); *B01J 37/04* (2013.01); *B01J 37/06* (2013.01); *B01J 37/08* (2013.01); *B01J 37/10* (2013.01); *C01G 39/00* (2013.01); *C01G 41/006* (2013.01); *C07C 51/235* (2013.01); *C07C 51/252* (2013.01); *C08F 220/06* (2013.01); *B01J 2523/00* (2013.01); *C01P 2002/72* (2013.01); *C01P 2006/12* (2013.01)

(58) Field of Classification Search
CPC ....  C07C 51/16; C07C 51/252; C07C 51/235; C07C 57/04; B01J 2523/17; B01J 2523/55; B01J 2523/68; B01J 2523/69; B01J 23/002; B01J 23/30; B01J 23/8885; B01J 35/002; B01J 35/023; B01J 35/1014; B01J 37/0009; B01J 37/0036; B01J 37/0045; B01J 37/0221; B01J 37/0223; B01J 37/033; B01J 37/04; B01J 37/06; B01J 37/08; B01J 37/10; C01G 39/00; C01G 41/006; C01P 2002/72; C01P 2006/12; C08F 220/06
USPC .................................................. 562/532, 535
See application file for complete search history.

(56) References Cited

U.S. PATENT DOCUMENTS

| | | | |
|---|---|---|---|
| 3,147,084 A | | 9/1964 | Franzen et al. |
| 3,567,773 A | * | 3/1971 | Yamaguchi et al. .......... 562/535 |

(Continued)

FOREIGN PATENT DOCUMENTS

| | | |
|---|---|---|
| DE | 2 201 528 A1 | 11/1972 |
| DE | 25 13 405 A1 | 10/1976 |

(Continued)

OTHER PUBLICATIONS

English translation of Dieterle et al. from a website titled Espacenet, translated on Apr. 25, 2014.*

(Continued)

*Primary Examiner* — Yevegeny Valenrod
*Assistant Examiner* — Blaine G Doletski
(74) *Attorney, Agent, or Firm* — Oblon, McClelland, Maier & Neustadt, L.L.P.

(57) ABSTRACT

A process for preparing (meth)acrylic acid by heterogeneously catalyzed gas phase partial oxidation of (meth)acrolein over a multimetal oxide composition which comprises the elements Mo, V and W and is obtained by a hydrothermal preparation route, and the multimetal oxide composition obtainable by this preparation route.

14 Claims, 7 Drawing Sheets

(51) Int. Cl.
   *B01J 23/00*    (2006.01)
   *C07C 51/235*   (2006.01)

(56) References Cited

U.S. PATENT DOCUMENTS

| | | | |
|---|---|---|---|
| 3,956,377 A * | 5/1976 | Dolhyj et al. | 562/535 |
| 4,146,574 A | 3/1979 | Onoda et al. | |
| 6,888,024 B2 | 5/2005 | Dieterle et al. | |
| 2004/0062870 A1 | 4/2004 | Dieterle et al. | |
| 2005/0215818 A1 | 9/2005 | Yunoki et al. | |
| 2005/0277546 A1* | 12/2005 | Hibst et al. | 502/312 |
| 2008/0214863 A1 | 9/2008 | Cremer et al. | |
| 2008/0269521 A1* | 10/2008 | Hammon et al. | 562/532 |
| 2009/0005593 A1 | 1/2009 | Yunoki et al. | |

FOREIGN PATENT DOCUMENTS

| | | |
|---|---|---|
| DE | 28 30 765 A1 | 1/1980 |
| DE | 29 09 671 A1 | 10/1980 |
| DE | 30 30 243 A1 | 3/1982 |
| DE | 44 31 949 A1 | 3/1995 |
| DE | 199 10 506 A1 | 9/2000 |
| DE | 199 10 508 A1 | 9/2000 |
| DE | 199 27 624 A1 | 12/2000 |
| DE | 199 48 241 A1 | 4/2001 |
| DE | 199 48 523 A1 | 4/2001 |
| DE | 199 52 964 A1 | 5/2001 |
| DE | 100 33 121 A1 | 1/2002 |
| DE | 100 51 419 A1 | 4/2002 |
| DE | 101 18 814 A1 | 10/2002 |
| DE | 103 21 398 A1 | 5/2004 |
| DE | 103 60 057 A1 | 7/2004 |
| DE | 103 50 822 A1 | 6/2005 |
| DE | 103 61 456 A1 | 7/2005 |
| DE | 10 2004 017 150 A1 | 10/2005 |
| DE | 10 2007 019 597 A1 | 5/2008 |
| DE | 10 2007 010 422 A1 | 9/2008 |
| DE | 10 2010 023 312 A1 | 12/2011 |
| EP | 0 383 224 A2 | 8/1990 |
| EP | 0 468 290 A1 | 1/1992 |
| EP | 0 700 714 A1 | 3/1996 |
| EP | 0 700 893 A1 | 3/1996 |
| EP | 0 714 700 A2 | 6/1996 |
| EP | 1 407 819 A2 | 4/2004 |
| JP | 58-96041 A | 6/1983 |
| JP | 6-227819 A | 8/1994 |
| JP | 2000-26123 A | 1/2000 |
| JP | 2007-260588 A | 10/2007 |
| WO | WO 02/083615 A1 | 10/2002 |
| WO | WO2004/031114 * | 4/2004 |
| WO | WO 2004/031114 A1 | 4/2004 |
| WO | WO 2005/047226 A1 | 5/2005 |
| WO | WO 2005/120702 A1 | 12/2005 |
| WO | WO 2006/094766 A1 | 9/2006 |
| WO | WO 2006/114428 A1 | 11/2006 |

OTHER PUBLICATIONS

International Search Report issued Sep. 30, 2013 in PCT/EP2013/058849 (with English translation of Category of Cited Documents).
U.S. Appl. No. 14/535,743, filed Nov. 7, 2014, Macht, et al.
U.S. Appl. No. 14/536,969, filed Nov. 10, 2014, Macht, et al.

* cited by examiner

PROCESS FOR HETEROGENEOUSLY CATALYZED GAS PHASE PARTIAL OXIDATION OF (METH)ACROLEIN TO (METH)ACRYLIC ACID

The present invention relates to a process for heterogeneously catalyzed gas phase partial oxidation of (meth)acrolein to (meth)acrylic acid over a catalytically active multimetal oxide composition of the general formula I

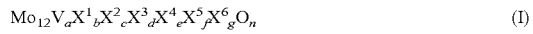

$$Mo_{12}V_a X^1_b X^2_c X^3_d X^4_e X^5_f X^6_g O_n \qquad (I)$$

in which the variables are each defined as follows:
$X^1$=W, Nb, Ta, Cr and/or Ce,
$X^2$=Cu, Ni, Co, Fe, Mn and/or Zn,
$X^3$=Sb, Te and/or Bi,
$X^4$=one or more alkali metals (Li, Na, K, Rb and/or Cs) and/or H,
$X^5$=one or more alkaline earth metals (Mg, Ca, Sr and/or Ba),
$X^6$=Si, Al, Ti and/or Zr,
a=1 to 6,
b=0.2 to 8,
c=0 to 18,
d=0 to 40,
e=0 to 4,
f=0 to 4,
g=0 to 40, and
n=a number which is determined by the valency and frequency of the elements in I other than oxygen.

(Meth)acrylic acid is used in this document as abbreviated notation for "acrylic acid and/or methacrylic acid".

(Meth)acrolein is used in this document as abbreviated notation for "acrolein and/or methacrolein".

Acrylic acid and methacrylic acid are important monomers which find use for preparation of polymers, for example, as such, in the form of their alkyl esters and/or in the form of their alkali metal salts. Depending on the specific (meth)acrylic monomers used to form the respective polymer, it can be used, for example, as an adhesive, or as Plexiglas®, or as a superabsorbent for water or aqueous solutions.

The preparation of (meth)acrylic acid by heterogeneously catalyzed gas phase partial oxidation of (meth)acrolein is common knowledge (cf., for example, WO 2004/031114 A1, EP 714700 A2, DE 4431949 A1, DE 3030243 A1, DE 3030243 A1 and the literature cited in these documents), and is of significance especially as the second oxidation stage in the preparation of (meth)acrylic acid by two-stage heterogeneously catalyzed gas phase partial oxidation proceeding from propene or from isobutene. It is also known that multimetal oxide compositions of the general formula I can be used as catalytically active compositions for the heterogeneously catalyzed partial gas phase oxidation of (meth)acrolein to (meth)acrylic acid (cf., for example, DE 102007010422 A1, DE 102010023312 A1, Applied Catalysis A: General 269 (2004), pages 53 to 61 and Applied Catalysis A: General 325 (2007), pages 237 to 243).

The starting materials used for preparation of these multimetal oxide active compositions are sources (starting compounds) of the elemental constituents other than oxygen in the desired multimetal oxide active composition in the respective stoichiometric ratio desired in the multimetal oxide active composition, and these are used to obtain a very intimate, preferably finely divided, dry mixture which is subsequently converted to an active oxide by thermal treatment. The sources may either already be oxides or may be those compounds which can be converted to oxides by heating, at least in the presence of oxygen.

The intimate mixing of the starting compounds (sources) can be effected in dry or wet form. If it is effected in dry form, the sources (starting compounds) are appropriately used in the form of fine powders and, after mixing (and optionally compaction for the purpose of powder coarsening), subjected to thermal treatment.

The intimate mixing in the prior art preparation processes, however, is preferably effected in wet form, and appropriately for application purposes in aqueous form. This involves mixing the starting compounds with one another in the form of a solution and/or suspension (e.g. aqueous solution and/or suspension). Subsequently, the wet composition (solution or suspension) (e.g. an aqueous composition (solution or suspension)) is dried and the resulting intimate dry mixture (optionally after intermediate compaction for the purpose of powder coarsening) is thermally treated. Particularly intimate dry mixtures are obtained in the mixing process described when the starting materials are exclusively sources (starting compounds) present in dissolved form. The drying operation is preferably effected by spray drying.

A characteristic feature of the prior art mode of production described is that all preparation steps (apart from any intermediate step for powder compaction employed for coarsening purposes) are conducted at atmospheric pressure.

However, a disadvantage of processes for heterogeneously catalyzed gas phase partial oxidation of (meth)acrolein to (meth)acrylic acid over multimetal oxide compositions of the general formula I obtainable as described as catalytically active compositions is that both the selectivity of target production formation (of (meth)acrylic acid formation) for a given conversion of the (meth)acrolein and the conversion of (meth)acrolein established for a given reaction temperature, and hence the activity of the catalytically active composition, are not entirely satisfactory. Both shortcomings are disadvantageous for a process for heterogeneously catalyzed partial gas phase oxidation of (meth)acrolein to (meth)acrylic acid in that they reduce the resulting yield of (meth)acrylic acid.

(Yield $A$ (mol %)=selectivity $S$ (mol %)×conversion $C$ (mol %)/100 mol %).

Catalysis Today 91-92 (2004), page 237 to 240, describes the hydrothermal preparation of a mixed oxide $Mo_{12}V_{3.48}O_x$ and the use thereof as a catalytically active composition for the heterogeneously catalyzed partial gas phase oxidation of acrolein to acrylic acid.

WO 2005/120702 A1 and EP 1407819 A2 relate to the hydrothermal preparation of multimetal oxide compositions which have, as base elements, likewise the elements Mo and V, but not the element W. Broadening of the base is undertaken in these documents primarily with the elements Nb and the elements Te and/or Sb. In both documents, the use of such multimetal oxide compositions as catalytically active compositions for a heterogeneously catalyzed partial gas phase oxidation of hydrocarbons, especially saturated hydrocarbons, is at the forefront. Usability of such mixed oxides as catalytically active compositions for a heterogeneously catalyzed partial gas phase oxidation of (meth)acrolein to (meth)acrylic acid is mentioned merely in passing in both documents.

A disadvantage of processes for heterogeneously catalyzed partial gas phase oxidation of (meth)acrolein to (meth)acrylic acid using the hydrothermally produced mixed oxides detailed above as catalytically active compositions is, however, that the catalytic performance declines at a comparatively early stage in the long-term operation of these processes.

It was therefore an object of the present invention to provide a process for heterogeneously catalyzed gas phase partial oxidation of (meth)acrolein to (meth)acrylic acid including the catalytically active multimetal oxide compositions required therefore, which has the described disadvantages of the corresponding prior art processes and of the active compositions used in these processes to a reduced degree at worst.

Accordingly, a process is provided for heterogeneously catalyzed gas phase partial oxidation of (meth)acrolein to (meth)acrylic acid over a catalytically active multimetal oxide composition of the general formula I

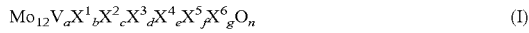

in which the variables are each defined as follows:
$X^1$=W, Nb, Ta, Cr and/or Ce,
$X^2$=Cu, Ni, Co, Fe, Mn and/or Zn,
$X^3$=Sb, Te and/or Bi,
$X^4$=one or more alkali metals (Li, Na, K, Rb and/or Cs) and/or H,
$X^5$=one or more alkaline earth metals (Mg, Ca, Sr and/or Ba),
$X^6$=Si, Al, Ti and/or Zr,
a=1 to 6,
b=0.2 to 8,
c=0 to 18,
d=0 to 40,
e=0 to 2,
f=0 to 4,
g=0 to 40, and
n=a number which is determined by the valency and frequency of the elements in I other than oxygen,
wherein
at least 50 mol % of the total molar amount of elements $X^1$ present in the multimetal oxide composition (I) is accounted for by the element W, and
the multimetal oxide composition (I) is prepared by a process in which a mixture of sources of the elemental constituents of the multimetal oxide composition (I) is subjected to a hydrothermal treatment in the presence of water in a pressure vessel (as an aqueous mixture), the newly forming solid is removed as a precursor composition and the precursor composition is converted to the catalytically active multimetal oxide composition (I) by thermal treatment.

Preferably in accordance with the invention, at least 60 mol %, more preferably at least 70 mol %, even more preferably at least 80 mol %, or at least 90 mol %, and at best at least 95 mol %, or 100 mol %, of the total molar amount of elements $X^1$ present in the multimetal oxide composition (I) is accounted for by the element W. These statements have general validity in this document irrespective of the rest of the composition of the multimetal oxide composition (I).

Advantageously, the stoichiometric coefficient b is 0.2 to 4 and particularly advantageously 0.2 to 3.

The stoichiometric coefficient c is preferably 0.5 to 18, more preferably 0.5 to 10 and most preferably 0.5 to 3.

The stoichiometric coefficient a is, advantageously in accordance with the invention, 1 to 5, and particularly advantageously 2 to 4.

Preferably in accordance with the invention, the stoichiometric coefficient d has values of 0 to 20, more preferably values of 0 to 10, and most preferably values of 0 to 2.

The stoichiometric coefficient e and the stoichiometric coefficient f are (each independently) advantageously 0 to 2.

The stoichiometric coefficient g is advantageously 0 to 15 and particularly advantageously 0 to 8.

$X^1$ is, advantageously in accordance with the invention, W, Nb and/or Cr, and particularly advantageously W and Nb, or (only) W.
$X^2$ is, advantageously in accordance with the invention, Cu, Ni, Co and/or Fe, and particularly advantageously Cu and/or Ni, or (only) Cu,
$X^3$ is, advantageously in accordance with the invention, Sb,
$X^4$ is, advantageously in accordance with the invention, Na, K and/or H,
$X^5$ is, preferably in accordance with the invention, Ca, Sr and/or Ba,
$X^6$ is, preferably in accordance with the invention, Si, Al and/or Ti, and more preferably Si and/or Al.

Preferred multimetal oxide compositions (I) include those in which the variables are each defined as follows:
$X^1$=W, Nb and/or Cr,
$X^2$=Cu, Ni, Co and/or Fe; preferably at least 50 mol %, better at least 70 mol %, and even better at least 90 mol % or 100 mol % of the total amount of elements $X^2$ present is accounted for by the element Cu,
$X^3$=Sb,
$X^4$=Na, K and/or H,
$X^5$=Ca, Sr and/or Ba,
$X^6$=Si, Al and/or Ti,
a=1 to 5,
b=0.2 to 4,
c=0.5 to 18,
d=0 to 10,
e=0 to 2,
f=0 to 2,
g=0 to 15, and
n=a number which is determined by the valency and frequency of the elements in the general formula I other than oxygen.

A group of multimetal oxide compositions (I) preferred in accordance with the invention satisfies the general stoichiometry II

in which the variables are each defined as follows:
$X^1$=W and/or Nb,
$X^2$=Cu and/or Ni; preferably at least 50 mol %, better at least 70 mol %, and even better at least 90 mol % or 100 mol % of the total molar amount of elements $X^2$ present is accounted for by the element Cu,
$X^4$=H,
$X^5$=Ca and/or Sr,
$X^6$=Si and/or Al,
a=2 to 4,
b=0.2 to 3,
c=0.5 to 3,
e=0 to 2,
f=0 to 0.5,
g=0 to 8, and
n=a number which is determined by the valency and frequency of the elements in the general formula II other than oxygen.

Another group of multimetal oxide compositions (I) preferred in accordance with the invention satisfies the general stoichiometry III

in which the variables are each defined as follows:
$X^4$=one or more alkali metals (Li, Na, K, Rb and/or Cs) and/or H,
$X^5$=one or more alkaline earth metals (Mg, Ca, Sr and/or Ba),
$X^6$=one or more elements from the group of Si, Al, Ti and Zr, a=2 to 4,
b=0.2 to 3,
c=0.5 to 2,
e=0 to 4,
f=0 to 4, with the proviso that the sum of e and f does not exceed 4,
g=0 to 40, and
n=a number which is determined by the valency and frequency of the elements in the general formula III other than oxygen (or, in other words: the stoichiometric coefficient of the element oxygen, which is determined by the stoichiometric coefficients of the elements other than oxygen and the valency thereof in the general formula III).

Preferably in accordance with the invention, the stoichiometric coefficient b in the general formula III is 0.5 to 2 and more preferably 0.75 to 1.5.

Preferably in accordance with the invention, the stoichiometric coefficient a in the general formula III is 2.5 to 3.5.

Preferably in accordance with the invention, the stoichiometric coefficient c in the general formula III is 1 to 1.5.

Elements $X^4$, $X^5$ and $X^6$ need not necessarily be part of the catalytically active multimetal oxide compositions of the general formula I (or of the general formula II or of the general formula III).

Elements $X^6$ within a catalytically active multimetal oxide active composition of the general formula I act essentially as inert diluents. As a result of incorporation thereof into the catalytically active multimetal oxide active compositions of the general formula I, the volume-specific activity thereof can be adjusted to the desired level. Frequently, the stoichiometric coefficient of $X^6$ in the inventive catalytically active multimetal oxide compositions of the general formula I (or general formula II or general formula III) is 0 to 15 or 0 to 8. The catalytically active multimetal oxide compositions of the general formula I (or general formula II or general formula III) to be used in accordance with the invention preferably do not comprise any element $X^6$. This statement also applies correspondingly to the elemental constituents $X^4$ and $X^5$, which have a moderating influence on the catalytic activity. Frequently, the sum of the stoichiometric coefficients e and f in the catalytically active multimetal oxide compositions of the general formula I (or general formula II or general formula III) to be employed in accordance with the invention will be 0 to 2, or 0 to 1, or 0 to 0.2.

Of course, in a multimetal oxide composition (II) or (III) too, at least 50 mol % of the total molar amount of elements $X^1$ present in each must be accounted for by the element W.

Preferably in accordance with the invention, in a multimetal oxide composition (II) or (III) too, at least 60 mol %, more preferably at least 70 mol %, even more preferably at least 80 mol %, or at least 90 mol %, and at best at least 95 mol % or 100 mol %, of the total molar amount of elements $X^1$ present in the multimetal oxide composition (II) or (III) is accounted for by the element W.

The hydrothermal preparation of multimetal oxide precursor compositions is familiar to those skilled in the art (cf., for example, Applied Catalysis A: 194 to 195 (2000), page 479 to 485; Kinetics and Catalysis, vol. 40, No. 3, 1999, page 401 to 404; Chem. Commun., 1999, page 517 to 518; JP-A 6/227819, JP-A 2000/26123 and DE 10033121 A1).

In particular (especially in this document), this is understood to mean the thermal treatment of a preferably intimate mixture of sources of the desired multimetal oxide composition I (or II or III) in the presence of water in a pressure vessel (autoclave) at temperatures in the range of >100° C. to 600° C. (preferably ≥110° C. to 400° C. and more preferably ≥130° C. to 300° C.) to form steam at superatmospheric pressure.

The pressure range of the working pressure (or steam pressure) which exists in the autoclave (in the gas phase) extends typically (from, for example, ≥200 kPa or from ≥500 kPa) to up to 50 MPa, preferably to up to 25 MPa or up to 22 MPa and more preferably up to 15 MPa (0.1013 MPa=1 atm). A possible representative working pressure (or steam pressure) is 2.5 MPa. It will be appreciated that it is also possible in accordance with the invention to employ temperatures above 600° C. and working pressures (or steam pressures) above 50 MPa, but this is less appropriate in application terms. Advantageously, the gas atmosphere in the autoclave during the hydrothermal treatment consists to an extent of at least 30% by volume, preferably to an extent of at least 50% by volume, more preferably to an extent of at least 75% by volume and even more preferably to an extent of at least 90% by volume, or to an extent of at least 95% by volume, or to an extent of at least 99% by volume, or exclusively of steam. Possible further constituents of the gas atmosphere present in the autoclave during the hydrothermal treatment include, for example, inert gases such as molecular nitrogen and noble gases (e.g. Ar, He). It will be appreciated, however, that molecular oxygen may also be a constituent of the aforementioned gas atmosphere. Further possible constituents of the gas atmosphere present during the hydrothermal treatment in the autoclave are gaseous decomposition products, for example ammonia, which can form in the course of a thermal decomposition of corresponding sources (for example comprising ammonium ions) used as part of the desired multimetal oxide composition I (or II or III).

Particularly advantageously, the inventive hydrothermal treatment is effected under those conditions under which steam and liquid water coexist (in the autoclave, in the pressure vessel). This is possible within the temperature range from >100° C. to 374.15° C. (critical temperature of water) with employment of the appropriate pressures.

The amounts of water are appropriately such that the liquid phase, during the hydrothermal treatment, is capable of absorbing the total amount of the starting compounds (sources) in suspension and/or solution (the latter being preferable in accordance with the invention over the suspension) (preferably also based on 25° C. and 101.3 kPa).

However, also possible in accordance with the invention is a hydrothermal procedure in which the (preferably intimate) mixture of the starting compounds fully takes up (absorbs) any amount of liquid water present at equilibrium in the course of hydrothermal treatment with the steam.

Advantageously in accordance with the invention, the hydrothermal treatment is effected at autoclave temperatures of >100° C. to 300° C., preferably at temperatures of 150° C. to 250° C. and more preferably at 160° C. to 190° C. (for example at 175° C.).

Based on the total amount of water and sources of the elemental constituents of the desired multimetal oxide composition I (or II or III) present in the autoclave (in the pressure vessel) during the hydrothermal treatment, the proportion by weight of the total amount of the latter in the autoclave, in accordance with the invention, is generally at least 1% by weight. Typically, the aforementioned proportion by weight is not above 90% by weight. Typically, corresponding proportions by weight are from 3 to 60% by weight, or from 5 to 30% by weight, frequently from 5 to 15% by weight. If one of the sources used (starting compounds) comprises, for example, hydrate water, this is not counted with the proportion by weight of the sources but with the proportion by weight of the water. In other words, the above proportion by weight of the total amount of starting compounds (sources) present in the autoclave is calculated "water-free".

As well as water and the sources of the elemental constituents other than oxygen in the desired multimetal oxide composition I (or II or III), the aqueous mixture to be treated hydrothermally in the autoclave (pressure vessel) (the aqueous mixture to be treated) may also comprise assistants, for example setting agents to adjust the pH thereof.

Based on a temperature of 25° C. and a pressure of 101.3 kPa (=1 atm), the pH of the aqueous mixture to be treated hydrothermally (prior to commencement of the hydrothermal treatment), advantageously in accordance with the invention, is at values of <7, particularly advantageously at values of ≤6 or ≤5, and very particularly advantageously at values of ≤4 or ≤3. Normally, the aforementioned pH, however, is at the values of ≥0. Very particularly advantageously in accordance with the invention, the aforementioned pH is ≥1 and ≤3, or ≥1.5 and ≤2.5. The pH values reported and pH determinations conducted in this document are based, unless explicitly stated otherwise, on a determination with a Checker® pH electrode HI 98103 from HANNA Instruments Deutschland GmbH, D-77694 Kehl. These have been calibrated before each measurement with the aid of two aqueous buffer solutions, the pH values of which under the corresponding conditions were 7.01 and 4.01 (Technical Buffer, Model TEP 7 (catalogue number 108702) and TEP 4 (catalogue number 108700) from WTW (Wissenschaftlich Technische Werkstätten GmbH) in D-82362 Weilheim).

Possible setting agents for establishing the aforementioned pH include, in particular, strong organic and strong inorganic acids (of the Brønsted type). Examples include nitric acid and sulfuric acid. Preferably in accordance with the invention, the setting agent used for the aforementioned pH is dilute sulfuric acid (concentration≈1 mol/l at 25° C., 101.3 kPa). Generally, strong acids favorable for the inventive purposes are those which are decomposed to gaseous compounds at elevated temperatures.

Salts such as ammonium carbonate, ammonium acetate, ammonium formate, ammonium nitrate, ammonium chloride or ammonium sulfate, for example, may likewise be part of the aqueous mixture to be treated hydrothermally. These can help to influence the ionic strength of the liquid aqueous medium. Preference is given to those mediators of the aforementioned ionic strength which are decomposed to gaseous compounds under the action of elevated temperatures.

During the inventive hydrothermal treatment, the aqueous mixture present in the pressure vessel may either be stirred or not stirred. Preference is given in accordance with the invention to stirring.

Useful sources for the elemental constituents of the relevant multimetal oxide composition generally include those compounds which are already oxides and/or those compounds which can be converted to oxides by heating, at least in the presence of molecular oxygen.

Starting compounds (sources) of the elemental constituents of the multimetal oxide composition (I) especially useful for the inventive hydrothermal preparation variant are all of those which are capable of forming oxides and/or hydroxides in the course of heating under elevated pressure with water. Of course, the starting compounds used partly or exclusively for the inventive hydrothermal treatment may also be oxides and/or hydroxides of the elemental constituents.

Sources suitable in accordance with the invention for the element Mo are, for example, molybdenum oxides such as molybdenum trioxide, molybdenum halides such as molybdenum chloride, and molybdates such as ammonium heptamolybdate (e.g. the tetrahydrate thereof). Ammonium heptamolybdate and the hydrates thereof are Mo sources particularly preferred in accordance with the invention.

Sources suitable in accordance with the invention for the element V are, for example, vanadyl acetylacetonate, vanadates such as ammonium metavanadate, vanadium oxides such as vanadium pentoxide ($V_2O_5$), and vanadium halides and oxide halides such as $VOCl_3$. Appropriately in accordance with the invention, the vanadium starting compounds also used are those which comprise the vanadium in the +4 oxidation state. A V source particularly preferred in accordance with the invention is vanadyl sulfate, and hydrates thereof.

The sources used for the element W may, in accordance with the invention, for example, be oxides of tungsten, for example $W_2O_3$, $WO_2$ and $WO_3$. Further tungsten starting compounds suitable in accordance with the invention are tungsten(VI) chloride, tungsten carbide and tungsten(IV) sulfide. Preferred W sources for the hydrothermal preparation process according to the invention, however, are the tungstates thereof or the acids derived therefrom. W sources particularly preferred for the inventive purposes are ammonium paratungstate and ammonium metavanadate, and hydrates thereof.

Useful sources for the elemental constituent Cu for the inventive purposes are especially copper(II) salts such as copper(II) sulfate, copper(II) nitrate and copper(II) acetate, and hydrates thereof.

Sources suitable in accordance with the invention for the elements tellurium are tellurium oxides such as tellurium dioxide, metallic tellurium, tellurium halides such as $TeCl_2$, but also tellurium acids such as orthotelluric acid $H_6TeO_6$.

Advantageous antimony starting compounds are antimony halides such as $SbCl_3$, antimony oxides such as antimony trioxide ($Sb_2O_3$), antimony acids such as $HSb(OH)_6$, but also antimony oxide salts such as antimony oxide sulfate [$(SbO_2)SO_4$].

Niobium sources suitable in accordance with the invention are, for example, niobium oxides such as niobium pentoxide ($Nb_2O_5$), niobium oxide halides such as $NbOCl_3$, niobium halides such as $NbCl_5$, but also complex compounds of niobium and organic carboxylic acids and/or dicarboxylic acids, for example oxalates and alkoxides.

With regard to the other possible elemental constituents of a multimetal oxide I (or II or III), useful starting compounds suitable in accordance with the invention with regards to the relevant hydrothermal treatment are in particular the halides, nitrates, formates, oxalates, acetates, carbonates and/or hydroxides thereof. Starting compounds suitable in accordance with the invention are also oxo compounds of these elemental constituents, for example the metalates thereof or the acids derived therefrom, or ammonium salts derived from these acids.

It will be appreciated that useful sources of the elemental constituents also include, for example, mixed oxides (or other mixed salts) which comprise more than one elemental constituent and may themselves have been obtained by a hydrothermal route.

In principle, useful sources also include multimetal oxides of the general stoichiometry I (or II or III) which have been obtained in a manner known per se (i.e. conventionally) by the known prior art preparation processes (for example as described in documents DE 102010023312 A1 and EP 714700 A2, and the prior art documents acknowledged in these two documents). As already detailed at the outset of this document, the starting materials are sources (starting compounds) of the elemental constituents other than oxygen in the desired multimetal oxide active composition in the respective stoichiometric ratio desired in the multimetal oxide active composition, and these are used to obtain a very intimate, preferably finely divided, dry mixture which is subsequently converted to an active oxide by non-hydrothermal thermal treatment. The sources may either already be oxides or those compounds which can be converted to oxides by heating, at least in the presence of oxygen.

The source used for the process according to the invention may also be a conventionally produced multimetal oxide of the general stoichiometry I (or II or III) which has already been used for catalysis of a heterogeneously catalyzed gas phase partial oxidation of (meth)acrolein to (meth)acrylic acid and has been deactivated in long-term operation thereof (cf. WO 2005/047226 A1). In this case, the employment of the process according to the invention generally brings about regeneration (reactivation) of the deactivated multimetal oxide composition. It will be appreciated that this may also be applied as an active composition shell on the surface of an inert molding (and form an eggshell catalyst together therewith).

The inventive hydrothermal treatment generally lasts for a period of a few minutes or hours up to a few days. A typical period is from 0.5 h to 100 h, frequently from 5 h to 80 h or from 10 h to 50 h or from 20 h to 50 h.

Appropriately in application terms, the autoclave to be used for the hydrothermal treatment is lined on the inside with Teflon® (coated with Teflon (=polytetrafluoroethylene)). In this way, contamination of the aqueous mixture to be treated hydrothermally with the pressure-resistant steel from which the pressure vessel is otherwise normally manufactured is reliably ruled out.

Prior to the inventive hydrothermal treatment, the autoclave, optionally including the aqueous mixture present, can be evacuated. Subsequently, it can be filled with inert gas ($N_2$, noble gas (e.g. Ar)) before the temperature is increased. The two measures can also be omitted (the latter is generally less advantageous particularly for the long-term stability of the autoclave). Of course, the aqueous mixture to be treated hydrothermally, prior to commencement of the hydrothermal treatment, can additionally or alternatively be purged with inert gas.

Appropriately in application terms, the aforementioned inert gases can also be utilized for establishment of superatmospheric pressure even prior to commencement of the actual hydrothermal treatment in the autoclave.

After the hydrothermal treatment has ended, the autoclave can be quenched to room temperature (typically 25° C.) or brought gradually to room temperature, i.e. over a prolonged period (for example of its own accord).

Preferably, after a cooling as described above, the autoclave can be opened and the solids which have newly formed in the course of the hydrothermal treatment can be removed from the remaining contents of the pressure vessel. In a simple manner, the removal can be effected, for example, by filtration or another mechanical separating operation (for example centrifugation).

The solids removed constitute a precursor composition for the desired catalytically active multimetal oxide I (or II or III). In favorable cases, this precursor composition may already display the desired catalytic activity.

Normally, the precursor composition removed, however, is additionally treated thermally before it finds use as a catalytically active multimetal oxide composition I (or II or III) for a process for heterogeneously catalyzed gas phase partial oxidation of (meth)acrolein to (meth)acrylic acid.

The starting stoichiometry of the aqueous mixture of sources of the relevant elemental constituents which is to be treated hydrothermally in each case in accordance with the invention and the stoichiometry of the resulting precursor composition need not necessarily correspond entirely. In general, however, they will be similar. The corresponding relationship between the two can be determined in a few preliminary tests in each case.

In principle, in the process according to the invention, the thermal treatment employed for the precursor composition may also be the heterogeneously catalyzed gas phase partial oxidation of (meth)acrolein to (meth)acrylic acid itself. In this case, the thermal treatment is effectively effected at reaction temperature and under (standing or flowing) reaction gas mixture as the calcination atmosphere. The transition to the catalytically active multimetal oxide composition is effected in this case effectively as a prolonged formatting. If the source used for the process according to the invention is a conventionally prepared multimetal oxide of the general stoichiometry I (or II or III), it is generally sufficient to employ drying of the precursor composition obtained as the thermal treatment, the temperatures typically being in the range from 100 to 200° C. or 100 to 150° C.

Typically, the thermal treatment of the precursor composition is effected, however, at temperatures above that temperature which has been employed in the course of hydrothermal treatment.

Apart from the warmup phase of the precursor composition to the required temperatures, the thermal treatment (the calcination) of the precursor composition is effected in a manner appropriate in accordance with the invention at a temperature of 300 to 700° C., frequently at a temperature of 350 to 650° C., or 400 to 600° C. The thermal treatment can be effected either under reduced pressure or under a gaseous atmosphere. It can be conducted under an oxidizing, reducing and/or inert gas atmosphere. A useful oxidizing gas atmosphere for the thermal treatment of the precursor composition is, for example, air, molecular oxygen-enriched air or molecular oxygen-depleted air (it will be appreciated that any other mixture of molecular oxygen and an inert gas can also be employed as an oxidizing gas atmosphere). Preferably, the thermal treatment of the precursor composition, in accordance with the invention, is conducted under an inert atmosphere, i.e., for example, under molecular nitrogen and/or noble gas. "Inert" means that the content in the gas atmosphere of $O_2$ and reducing constituents is in each case ≤3% by volume, better ≤1% by volume, even better ≤0.1% by volume and at best 0% by volume.

When the thermal treatment of the precursor composition is effected under gaseous atmosphere, this may either be stationary or flowing. Overall, the thermal treatment of the precursor composition may last for up to 24 h or more. Frequently, the thermal treatment of the precursor composition extends to a period of 0.5 h to 10 h, or of 1 h to 5 h. Elevated temperatures are normally associated with shorter durations of thermal treatment and, at lower temperatures, generally longer periods of thermal treatment are employed. High temperatures and long treatment times generally reduce the specific surface area of the catalytically active multimetal oxide composition I (or II or III) which results in the course of thermal treatment of the precursor composition.

The removal of the precursor composition after the hydrothermal treatment of the corresponding aqueous mixture has ended from the remaining contents of the pressure vessel may comprise, in addition to, for example, a mechanical separating operation (for example filtration), also a washing operation on the precursor composition which has been removed, for example, by mechanical means with a (suitable) liquid. In the course of such a washing operation, residual starting constituents (or setting agent used to adjust the pH) which still remain adhering on the surfaces of the precursor composition from the hydrothermal treatment, and/or by-products formed, can be removed advantageously in accordance with the invention.

Useful washing liquids of this kind include, for example, water, organic acids or aqueous solutions thereof (e.g. oxalic acid, formic acid, acetic acid and tartaric acid) and inorganic acids and aqueous solutions thereof (e.g. sulfuric acid, perchloric acid, hydrochloric acid, nitric acid and/or telluric acid), but also alcohols, alcoholic solutions of the aforementioned acids or hydrogen peroxide and aqueous solutions thereof.

It will be appreciated that mixtures of the aforementioned wash liquids can also be used for washing. Preferably in accordance with the invention, the wash liquid used is a solution of oxalic acid in water. A suitable oxalic acid content of such a solution may, for example, be 0.4 mol of oxalic acid/l of solution (at 25° C. and 101.3 kPa). Advantageously in accordance with the invention, the washing is effected at an elevated temperature (e.g. 70 to 80° C.). Appropriately in accordance with the invention, this is followed by washing with water.

The washing may be followed, after the removal of the wash liquid, by the thermal treatment of the precursor composition to be performed as already described.

For the sake of good order, it should be stated at this point that the thermal treatment of the precursor composition can also be commenced initially under oxidizing (molecular oxygen comprising) atmosphere (e.g. under air) and then continued under inert gas atmosphere (or vice versa) etc.

It will be appreciated that the precursor composition, prior to thermal treatment thereof, can also be comminuted to powder or spall.

The catalytically active multimetal oxide compositions I (or II or III) obtainable in accordance with the invention can be used as such (for example comminuted to powder or to spall) or else shaped to shaped bodies as catalytic active compositions for the heterogeneously catalyzed partial gas phase oxidation of (meth)acrolein to (meth)acrylic acid. The catalyst bed may be a fixed bed, a moving bed or a fluidized bed.

In the case of unsupported catalysts, the shaping can be effected, for example, by extrusion or tabletting, and, in the case of eggshell catalysts, by application to a support body, as described in DE 10118814 A1, or PCT/EP/02/04073, or DE 10051419 A1, or DE 102010023312 A1, or DE 102007010422 A1, or EP 714700 A2.

The support bodies to be used for the multimetal oxide compositions I (or II or III) obtainable in accordance with the invention in the case of eggshell catalysts are preferably chemically inert. In other words, they essentially do not intervene in the course of the heterogeneously catalyzed partial gas phase oxidation of (meth)acrolein to (meth)acrylic acid.

Useful materials for the support bodies include, in accordance with the invention, especially aluminum oxide, silicon dioxide, silicates such as clay, kaolin, steatite (preferably C-220 steatite from CeramTec (DE), or preferably with a low water-soluble alkali content), pumice, aluminum silicate, magnesium silicate, silicon carbide and zirconium dioxide.

The surface of the support body may be either smooth or rough. Advantageously, the surface of the support body is rough, since an elevated surface roughness generally causes increased adhesive strength of the active composition shell applied.

Useful support bodies with distinct surface roughness include especially support bodies which have a grit layer on their surface.

The surface roughness $R_z$ of the support body is preferably in the range from 30 to 100 μm, more preferably in the range from 50 to 70 μm (determined to DIN 4768 sheet 1 with a "Hommel Tester for DIN ISO surface parameters" from Hornmelwerke). Particular preference is given to rough-surface support bodies from CeramTec made from C220 steatite.

The support materials may be porous or nonporous. The support material is preferably nonporous (the total volume of the pores based on the volume of the support body is advantageously ≤1% by volume).

The support bodies may be regular or irregular in shape, preference being given to support bodies of regular shape.

The longest dimension of the support bodies is normally in the range from 1 to 10 mm (the longest dimension is the longest direct straight line connecting two points on the surface of a support body).

Preference is given in accordance with the invention to spheres or cylinders, especially hollow cylinders (rings), as support bodies. Favorable diameters for support spheres are 1 to 4 mm. If cylinders are used as support bodies, the length thereof is preferably 2 to 10 mm and the external diameter thereof preferably 4 to 10 mm. In the case of rings, the wall thickness is additionally typically 1 to 4 mm. Annular support bodies suitable in accordance with the invention may also have a length of 3 to 6 mm, an external diameter of 4 to 8 mm and a wall thickness of 1 to 2 mm. Also possible, however, is a support ring geometry of 7 mm×3 mm×4 mm, or of 5 mm×3 mm×2 mm (external diameter×length×internal diameter).

The thickness of the active multimetal oxide composition shell on the surface of the support bodies of inventive eggshell catalysts is typically 10 to 1000 μm. It may also be 50 to 700 μm, 100 to 600 μm or 150 to 500 μm. Possible shell thicknesses are also 10 to 500 μm, 100 to 500 μm or 150 to 300 μm.

Inventive eggshell catalysts can be produced in the simplest manner by preforming the desired multimetal oxide composition of the general formula I, converting it to a finely divided form and finally applying it to the surface of the support body with the aid of a liquid binder.

For this purpose, the surface of the support body is appropriately moistened in a controlled manner with the liquid binder (for example by spraying) and a layer of the active composition is fixed on the moistened surface by contacting the support bodies thus moistened with finely divided catalytically active multimetal oxide I (or II or III) obtained in accordance with the invention (for example, dust the moistened support bodies with active composition powder as described in EP 714700 A2). Subsequently, the coated support bodies are dried and the adhesion liquid is at least partly removed (for example by passing hot gas through; cf. WO 2006/094766). "Moisten in a controlled manner" means in this context that the support surface is appropriately moistened in such a way that it has adsorbed liquid binder but no liquid phase as such is visible on the support surface. If the support surface is too moist, the finely divided, catalytically active multimetal oxide composition agglomerates to form separate agglomerates rather than attaching to the surface. Detailed information on this subject can be found in DE 2909671 A1 and in DE 10051419 A1. Of course, the operation can be repeated periodically to achieve an increased layer thickness. In this case, the coated base body becomes the new "support body" etc. However, it is also possible to employ all other application processes acknowledged as prior art in EP 714700 A2 for preparation of inventive eggshell catalysts. In principle, inventive eggshell catalysts can be also be produced by first applying finely divided precursor composition to the surface of the support body and performing the thermal treatment of the precursor composition to give the catalytically active multimetal oxide composition of the general formula I (or II or III) only subsequently, i.e. with it already present on the surface of the support body.

Examples of useful liquid binders include water, an organic solvent or a solution of an organic substance (for example of an organic solvent) in water or in an organic solvent. Examples of organic binders include mono- or polyhydric organic alcohols, for example ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, and mono- or polyfunctional organic amides such as formamide. Suitable organic binder promoters soluble in water, in an organic liquid or in a mixture of water and an organic liquid are, for example, monosaccharides and oligosaccharides such as glucose, fructose, sucrose and/or lactose.

Particularly advantageously, the liquid binder used is a solution consisting of 20 to 90% by weight of water and 10 to 80% by weight of an organic compound. The organic component in the aforementioned liquid binders is preferably 10 to 50% and more preferably 20 to 30% by weight. Very particularly preferred liquid binders are solutions consisting of 20 to 90% by weight of water and 10 to 80% by weight of glycerol. Advantageously, the glycerol component in these aqueous solutions is 10 to 50% by weight and more preferably 20 to 30% by weight. One reason for the advantage of binders preferred in accordance with the invention is that they are capable of wetting both the finely divided active composition (or the finely divided precursor composition) and the support bodies in an entirely satisfactory manner.

The fineness of the catalytically active multimetal oxide composition of the general formula I (or II or III) to be applied to the surface of the support body, or of the precursor composition thereof, is of course matched to the desired layer thickness. Suitable active composition powders for the shell thickness range from 100 to 500 μm are, for example, those of which at least 50% of the total number of powder particles pass through the mesh size of 1 to 20 μm or alternatively 1 to 10 μm and where the numerical proportion of particles having a longest dimension above 50 μm is less than 10%. For the rest, the statements made on page 18 of WO 2005/120702 A1 apply correspondingly.

Preferably in accordance with the invention, inventive eggshell catalysts will be produced by the mode of preparation described and executed by way of example in EP 714700 A2. An aqueous solution of 75% by weight of water and 25% by weight of glycerol is the preferred binder. The process for thermal treatment of the precursor composition will, advantageously in accordance with the invention, be conducted by the procedure described and executed by way of example in DE 10360057 A1.

In order to additionally increase the long-term stability of an inventive eggshell catalyst, following the teaching of US 2008/214863 A1, rather than solely finely divided multimetal oxide composition I (or II or III), it is advantageously possible to apply to the surface of the support body a finely divided mixture thereof with a finely divided substance S from the group consisting of oxides of molybdenum and of compounds of molybdenum from which an oxide of molybdenum is formed under the action of elevated temperature and molecular oxygen.

Remarkably, multimetal oxide compositions of the general formula I (or II or III) prepared in accordance with the invention are characterized by an elevated specific surface area SA (BET surface area, molecular nitrogen).

In general, SA ≥15 m$^2$/g or ≥20 m$^2$/g; in many cases, SA is at values of ≥25 m$^2$/g, or at values of ≥30 m$^2$/g. Normally, SA will not exceed 150 m$^2$/g. In some cases, the values achieved for SA are ≤100 m$^2$/g, or ≤60 m$^2$/g or ≤50 m$^2$/g or ≤40 m$^2$/g. Particularly high values for SA are obtained when a conventionally prepared multimetal oxide of the general stoichiometry I (or II or III) as the source in the process according to the invention is "hydrothermally after treated".

To determine specific surface areas SA, sample weights of about 1 g were used. The determinations themselves were effected with an AUTOSORB 3B instrument from Quantachrome GmbH & Co. KG in DE-85235 Odelzhausen. To prepare for the actual measurement, the sample to be analyzed in each case was first held under high vacuum at 200° C. for 10 h and then purged with helium at 200° C. over 24 h. This was followed by the nitrogen adsorption at −196° C.

In general, multimetal oxide compositions of the general formula I (or II or III) prepared in accordance with the invention have not an X-ray-amorphous but a semicrystalline structure (i.e. the X-ray diffractogram has only few (generally fewer than 5) separate diffraction lines (reflections) whose half-height width on the 2 theta scale is ≤4° (the half-height width is as defined in DE 10321398 A1)) (in this document, figures given for X-ray diffractograms relate in each case to a powder diffractogram using Cu—K$_{\alpha 1}$ radiation ($\lambda$=1.540698 Å); the diffractometer used was a Stadi P instrument from Stoe & Cie GmbH in D-64295 Darmstadt, which monochromatized the radiation used with a Ge [1,1,1] single crystal; the radiation reflected by the sample was recorded with a location-sensitive detector (Mythen 1K detector from Dectris Ltd. in CH-5400 Baden)). The assignment of a crystal structure is normally impossible.

The catalytically active multimetal oxide compositions of the general formula I (or II or III) obtainable in accordance with the invention, and catalysts equipped (modified) therewith or shaped therefrom, are especially suitable as catalysts for a process for heterogeneously catalyzed partial gas phase oxidation of (meth)acrolein to (meth)acrylic acid, and more preferably for a process for heterogeneously catalyzed partial gas phase oxidation of acrolein to acrylic acid. They are notable particularly in that a catalyst bed charged therewith, in the course of performance of the partial oxidation, has a high service life over which the target product is formed at high activity with high selectivity.

This is particularly true when the heterogeneously catalyzed partial gas phase oxidation of (meth)acrolein to (meth)acrylic acid is performed at high (meth)acrolein loads, as described, for example, by DE 10307983 A1, DE 19948523 A1 and DE 19910508 A1.

The heterogeneously catalyzed partial gas phase oxidation can be performed in a manner known per se. In other words, a reaction gas mixture comprising the (meth)acrolein, molecular oxygen and at least one inert diluent gas is conducted at elevated temperature through a catalyst bed whose catalysts have, as the active composition, at least one multimetal oxide composition of the general formula I (or II or III) and, during the residence time of the (meth)acrolein in the catalyst bed, it is converted to (meth)acrylic acid. A catalyst bed preferred in accordance with the invention is a fixed catalyst bed. In principle, for the process according to the invention, however, a fluidized bed or a moving bed are also useful. In general, steam as a constituent of the reaction gas mixture leads to an improvement in selectivity and activity.

Otherwise, inert diluent gases with elevated molar specific heat, for example n-propane or $CO_2$, are advantageous.

Particularly suitable for performance of the gas phase partial oxidation of (meth)acrolein are heat exchanger reactors.

A heat exchanger reactor has at least one primary space and at least one secondary space, the two being divided from one another by a dividing wall. In the at least one primary space is positioned the catalyst charge which comprises at least one multimetal oxide composition of the general formula I (or II or III), through which a reaction gas mixture comprising (meth)acrolein flows. At the same time, a fluid heat carrier flows through the secondary space and the heat exchange takes place between the two spaces through the dividing wall, this pursuing the purpose of controlling the temperature of the reaction gas mixture on the route thereof through the catalyst bed.

In general, the gas phase partial oxidation of (meth)acrolein is conducted in a shell-and-tube (heat exchanger) reactor having one or more temperature zones, as described, for example, by EP 700714 A1, EP 700893 A1, DE 19910508 A1, DE 19948523 A1, DE 19910506 A1, DE 19948241 A1, DE 2830765 A1, DE 2513405 A1, U.S. Pat. No. 3,147,084 A, DE 2201528 A1, EP 383224 A2, JP 2007-260588 A and JP 58096041 A.

A fixed catalyst bed is present here in the form of a corresponding bed of shaped catalyst bodies (optionally in a mixture with diluting inert shaped bodies) in the metal tubes (catalyst tubes) of the tube bundle reactor, and the temperature medium/media is/are conducted around the metal tubes (in the case of more than one temperature zone, a corresponding number of essentially spatially separate temperature media are conducted around the metal tubes). The temperature medium is generally a salt melt. The reaction gas mixture is conducted through the catalyst tubes.

Alternatively, the fixed catalyst bed may, for example, also be present in the spaces between thermoplates of a thermoplate reactor through which a heat carrier flows, as recommended, for example, by DE 102004017150 A1, DE 19952964 A1 and DE 10361456 A1.

The fixed catalyst bed may, as already stated, quite generally consist only of catalysts obtainable in accordance with the invention, but also of such catalysts diluted with inert shaped bodies. The inert shaped bodies used may, for example, be the shaped support bodies (support bodies) used for preparation of inventive eggshell catalysts. Upstream of and/or beyond the fixed catalyst bed may be a pure inert shaped body bed (such pure inert shaped body beds are not normally included in the calculation of the space velocity on the fixed catalyst bed with reaction gas or with a reaction gas component).

Catalyst tubes used in a shell-and-tube reactor are customarily manufactured from ferrite steel and typically have a wall thickness of 1 to 3 mm. The internal diameter thereof is generally 20 to 30 mm, frequently 21 to 26 mm. The length thereof is appropriately 2 to 4 m.

Appropriately in application terms, the number of catalyst tubes accommodated in the shell-and-tube vessel runs to at least 5000, preferably to at least 10 000. Frequently, the number of catalyst tubes accommodated in the reactor vessel is 15 000 to 40 000. Shell-and-tube reactors having a number of catalyst tubes above 50 000 are usually exceptional. Within the vessel, the catalyst tubes are normally arranged in homogeneous distribution (preferably 6 equidistant neighboring tubes per catalyst tube), and the distribution is appropriately selected such that the distance between the central internal axes of mutually closest catalyst tubes (called the catalyst tube pitch) is 35 to 45 mm (cf., for example, EP-B 468290 A1).

The heat exchange media used for shell-and-tube reactors are particularly favorably melts of salts such as potassium nitrate, potassium nitrite, sodium nitrite and/or sodium nitrate, or of low-melting metals such as sodium, mercury and alloys of various metals.

Charging of catalyst tubes in shell-and-tube reactors with catalysts obtainable in accordance with the invention is advantageous particularly when the shell-and-tube reactor is operated at a (meth)acrolein space velocity on the catalyst charge which is ≥135 l (STP)/l·h, or ≥150 l (STP)/l·h, or ≥160 l (STP)/l·h, or ≥170 l (STP)/l·h, or ≥180 l (STP)/l·h, or ≥200 l (STP)/l·h, or ≥220 l (STP)/l·h, or ≥240 l (STP)/l·h. Of course, such a catalyst charge is also advantageous at lower (e.g. ≤130 l (STP)/l·h, or ≤100 l (STP)/l·h, or ≤80 l (STP)/l·h, or ≤60 l (STP)/l·h) (meth)acrolein space velocities.

In general, the (meth)acrolein space velocity on the catalyst charge will, however, be ≤350 l (STP)/l·h, or ≤300 l (STP)/l·h, or ≤250 l (STP)/l·h (corresponding space velocities can also be implemented in thermoplate reactors).

The terms "space velocity" and "l (STP)" are used as defined in DE 19927624 A1.

The volume-specific activity of the fixed catalyst bed will generally be configured such that it increases in flow direction of the reaction gas.

This can be implemented in a simple manner, for example, by decreasing the dilution level of the fixed catalyst bed with inert shaped bodies in flow direction of the reaction gas.

Otherwise, the heterogeneously catalyzed partial oxidation with, for example, eggshell catalysts obtainable in accordance with the invention can quite generally be performed in all aspects as detailed, for example, by DE A 10350822 A1. The (meth)acrolein content in the reaction gas input mixture may, for example, be at values of 3 or 6 to 15% by volume, frequently 4 or 6 to 10% by volume, or 5 to 8% by volume (based in each case on the total volume).

The molar ratio of $O_2$:(meth)acrolein in the reaction gas input mixture will normally be ≥1. This ratio will typically be at values of ≤3. In many cases, the heterogeneously catalyzed (meth)acrolein partial oxidation to (meth)acrylic acid will be executed with a (meth)acrolein oxygen:steam:inert gas volume ratio (l(STP)) present in the reaction gas input mixture of 1:(1 to 3):(0 to 20):(3 to 30), preferably of 1:(1 to 3):(0.5 to 10):(7 to 10).

Useful inert diluent gases (these are gases or mixtures of such gases which, on single pass of the reaction gas mixture through the catalyst bed (e.g. fixed bed), remain chemically unchanged to an extent of at least 95 mol %, preferably to an extent of at least 97 mol % or to an extent of at least 99 mol %, and at best to an extent of 100 mol %) include $N_2$, $CO_2$, CO, noble gases, propane, ethane, methane, butane and/or pentane (i.e. each as the sole diluent gas or in a mixture with another inert diluent gas or with several others among these inert diluent gases). The reaction temperatures of such a heterogeneously catalyzed (meth)acrolein partial oxidation are typically in the range from 200 to 400° C., generally from 220 to 380° C., in many cases from 230 to 350° C., frequently from 245 to 285° C., or from 245 to 265° C. The working pressure is normally 101.3 to 350 kPa.

The (meth)acrolein conversion, based on a single pass of the reaction gas mixture through the, for example, fixed catalyst bed, is typically ≥90 mol %, or ≥96 mol %, frequently ≥98 mol %, and in many cases ≥99 mol %.

For the rest, the inventive partial oxidation process can be executed in a manner entirely corresponding to the recommendations and teachings of DE 102007019597 A1.

More particularly, the source used for the (meth)acrolein required for the inventive partial oxidation may directly be the (meth)acrolein-comprising product gas mixture from a heterogeneously catalyzed partial oxidation of a $C_3/C_4$ precursor compound (e.g. propene or isobutene) of (meth)acrolein to (meth)acrolein, without any need to remove the (meth)acrolein from such a product gas mixture beforehand.

The selectivity S of (meth)acrylic acid formation (mol %) is understood in this document to mean:

$$S = \frac{\text{Number of moles of (meth)acrolein converted to (meth)acrylic acid}}{\text{Number of moles of (meth)acrolein converted overall}} \times 100 \text{ mol \%}$$

(the conversions are each based on a single pass of the reaction gas mixture through the catalyst bed).

An active composition (catalyst) which leads to the same conversion at lower temperature under otherwise unchanged reaction conditions has a higher activity.

The conversion C of (meth)acrolein (mol %) is defined in a corresponding manner as:

$$C = \frac{\text{Number of moles of (meth)acrolein converted}}{\text{Number of moles of (meth)acrolein used}} \times 100 \text{ mol \%}.$$

The (meth)acrylic acid can be removed from the product gas mixture of the partial oxidation in a manner known per se, for example by first converting the (meth)acrylic acid to the condensed phase by absorptive and/or condensative measures. Subsequent thermal separation processes, for example rectification and/or crystallization, can subsequently isolate (meth)acrylic acid from the condensed phase in any desired purity (cf., for example, DE 602004924 T2 and WO 2006/114428 A1, and the prior art cited in these documents).

Thus, the present application comprises especially the following inventive embodiments:

1. A process for heterogeneously catalyzed gas phase partial oxidation of (meth)acrolein to (meth)acrylic acid over a catalytically active multimetal oxide composition of the general formula I $$Mo_{12}V_a X^1_b X^2_c X^3_d X^4_e X^5_f X^6_g O_n \qquad (I)$$

in which the variables are each defined as follows:
  $X^1$=W, Nb, Ta, Cr and/or Ce,
  $X^2$=Cu, Ni, Co, Fe, Mn and/or Zn,
  $X^3$=Sb, Te and/or Bi,
  $X^4$=one or more alkali metals (Li, Na, K, Rb and/or Cs) and/or H,
  $X^5$=one or more alkaline earth metals (Mg, Ca, Sr and/or Ba),
  $X^6$=Si, Al, Ti and/or Zr,
  a=1 to 6,
  b=0.2 to 8,
  c=0 to 18,
  d=0 to 40,
  e=0 to 4,
  f=0 to 4,
  g=0 to 40, and
  n=a number which is determined by the valency and frequency of the elements in I other than oxygen,
  wherein
    at least 50 mol % of the total molar amount of elements $X^1$ present in the multimetal oxide composition (I) is accounted for by the element W, and
    the multimetal oxide composition (I) is prepared by a process in which a mixture of sources of the elemental constituents of the multimetal oxide composition (I) is subjected to a hydrothermal treatment in the presence of water in a pressure vessel (as an aqueous mixture), the newly forming solid is removed as a precursor composition and the precursor composition is converted to the catalytically active multimetal oxide composition (I) by thermal treatment.

2. The process according to embodiment 1, wherein at least 60 mol % of the total molar amount of elements $X^1$ present in the multimetal oxide composition (I) is accounted for by the element W.

3. The process according to embodiment 1, wherein at least 70 mol % of the total molar amount of elements $X^1$ present in the multimetal oxide composition (I) is accounted for by the element W.

4. The process according to embodiment 1, wherein at least 80 mol % of the total molar amount of elements $X^1$ present in the multimetal oxide composition (I) is accounted for by the element W.

5. The process according to embodiment 1, wherein at least 90 mol % of the total molar amount of elements $X^1$ present in the multimetal oxide composition (I) is accounted for by the element W.

6. The process according to embodiment 1, wherein at least 95 mol % of the total molar amount of elements $X^1$ present in the multimetal oxide composition (I) is accounted for by the element W.

7. The process according to embodiment 1, wherein 100 mol % of the total molar amount of elements $X^1$ present in the multimetal oxide composition (I) is accounted for by the element W.

8. The process according to any of embodiments 1 to 7, wherein the stoichiometric coefficient b is 0.2 to 4.

9. The process according to any of embodiments 1 to 7, wherein the stoichiometric coefficient b is 0.2 to 3.

10. The process according to any of embodiments 1 to 9, wherein the stoichiometric coefficient c is 0.5 to 18.

11. The process according to any of embodiments 1 to 9, wherein the stoichiometric coefficient c is 0.5 to 10.

12. The process according to any of embodiments 1 to 9, wherein the stoichiometric coefficient c is 0.5 to 3.

13. The process according to any of embodiments 1 to 12, wherein the stoichiometric coefficient a is 1 to 5.

14. The process according to any of embodiments 1 to 13, wherein the stoichiometric coefficient a is 2 to 4.

15. The process according to any of embodiments 1 to 14, wherein the stoichiometric coefficient d is 0 to 20.

16. The process according to any of embodiments 1 to 14, wherein the stoichiometric coefficient d is 0 to 10.

17. The process according to any of embodiments 1 to 14, wherein the stoichiometric coefficient d is 0 to 2.

18. The process according to any of embodiments 1 to 17, wherein the stoichiometric coefficient e is 0 to 2.

19. The process according to any of embodiments 1 to 18, wherein the stoichiometric coefficient f is 0 to 2.

20. The process according to any of embodiments 1 to 19, wherein $X^1$=W, Nb and/or Cr.

21. The process according to any of embodiments 1 to 19, wherein $X^1$=W and Nb.

22. The process according to any of embodiments 1 to 19, wherein $X^1$=W.

23. The process according to any of embodiments 1 to 22, wherein $X^2$=Cu, Ni, Co and/or Fe.

24. The process according to any of embodiments 1 to 22, wherein $X^2$=Cu and/or Ni.

25. The process according to any of embodiments 1 to 22, wherein $X^2$=Cu.

26. The process according to any of embodiments 1 to 25, wherein $X^3$=Sb.
27. The process according to any of embodiments 1 to 26, wherein $X^4$=Na, K and/or H.
28. The process according to any of embodiments 1 to 27, wherein $X^5$=Ca, Sr and/or Ba.
29. The process according to any of embodiments 1 to 28, wherein $X^6$=Si, Al and/or Ti.
30. The process according to any of embodiments 1 to 28, wherein $X^6$=Si and/or Al.
31. The process according to any of embodiments 1 to 7, wherein the variables of the general formula I are each defined as follows:
$X^1$=W, Nb and/or Cr,
$X^2$=Cu, Ni, Co and/or Fe
$X^3$=Sb,
$X^4$=Na, K and/or H,
$X^5$=Ca, Sr and/or Ba,
$X^6$=Si, Al and/or Ti,
a=1 to 5,
b=0.2 to 4,
c=0.5 to 18,
d=0 to 10,
e=0 to 2,
f=0 to 2,
g=0 to 15, and
n=a number which is determined by the valency and frequency of the elements in the general formula I other than oxygen.
32. The process according to embodiment 31, wherein at least 50 mol % of the total molar amount of elements $X^2$ present in the multimetal oxide composition (I) is accounted for by the element Cu.
33. The process according to embodiment 31, wherein at least 70 mol % of the total molar amount of elements $X^2$ present in the multimetal oxide composition (I) is accounted for by the element Cu.
34. The process according to embodiment 31, wherein at least 90 mol % of the total molar amount of elements $X^2$ present in the multimetal oxide composition (I) is accounted for by the element Cu.
35. The process according to embodiment 31, wherein 100 mol % of the total molar amount of elements $X^2$ present in the multimetal oxide composition (I) is accounted for by the element Cu.
36. The process according to any of embodiments 1 to 7, wherein the catalytically active multimetal oxide composition satisfies the general stoichiometry II $$Mo_{12}V_aX^1_bX^2_cX^4_eX^5_fX^6_gO_n \qquad (II)$$

in which the variables are each defined as follows:
$X^1$=W and/or Nb,
$X^2$=Cu and/or Ni,
$X^4$=H,
$X^5$=Ca and/or Sr,
$X^6$=Si and/or Al,
a=2 to 4,
b=0.2 to 3,
c=0.5 to 3,
e=0 to 2,
f=0 to 0.5,
g=0 to 8, and
n=a number which is determined by the valency and frequency of the elements in the general formula II other than oxygen.

37. The process according to embodiment 36, wherein at least 50 mol % of the total molar amount of elements $X^2$ present in the multimetal oxide composition is accounted for by the element Cu.
38. The process according to embodiment 36, wherein at least 70 mol % of the total molar amount of elements $X^2$ present in the multimetal oxide composition is accounted for by the element Cu.
39. The process according to embodiment 36, wherein at least 90 mol % of the total molar amount of elements $X^2$ present in the multimetal oxide composition is accounted for by the element Cu.
40. The process according to embodiment 36, wherein 100 mol % of the total molar amount of elements $X^2$ present in the multimetal oxide composition is accounted for by the element Cu.
41. The process according to any of embodiments 1 to 7, wherein the catalytically active multimetal oxide composition satisfies the general stoichiometry III $$Mo_{12}V_aW_bCu_cX^4_eX^5_fX^6_gO_n \qquad (III)$$

in which the variables are each defined as follows:
$X^4$=one or more alkali metals (Li, Na, K, Rb and/or Cs) and/or H,
$X^5$=one or more alkaline earth metals (Mg, Ca, Sr and/or Ba),
$X^6$=one or more elements from the group of Si, Al, Ti and Zr,
a=2 to 4,
b=0.2 to 3,
c=0.5 to 2,
e=0 to 4,
f=0 to 4, with the proviso that the sum of e and f does not exceed 4,
g=0 to 40, and
n=a number which is determined by the valency and frequency of the elements in the general formula III other than oxygen.

42. The process according to embodiment 41, wherein the stoichiometric coefficient b is 0.5 to 2.
43. The process according to embodiment 41 or 42, wherein the stoichiometric coefficient a is 2.5 to 3.5.
44. The process according to any of embodiments 41 to 43, wherein the stoichiometric coefficient c is 1 to 1.5.
45. The process according to any of embodiments 1 to 44, wherein the hydrothermal treatment is effected at temperatures in the range of >100° C. to 600° C.
46. The process according to any of embodiments 1 to 45, wherein the hydrothermal treatment is effected at temperatures in the range of ≥110° C. to 400° C.
47. The process according to any of embodiments 1 to 46, wherein the hydrothermal treatment is effected at temperatures in the range of ≥130° C. to 300° C.
48. The process according to any of embodiments 1 to 47, wherein the hydrothermal treatment is effected at a superatmospheric working pressure of ≤50 MPa.
49. The process according to any of embodiments 1 to 48, wherein the hydrothermal treatment is effected at a working pressure of ≥200 kPa and ≤25 MPa or at a working pressure of ≥500 kPa and ≤22 MPa.
50. The process according to any of embodiments 1 to 49, wherein steam and liquid water coexist during the hydrothermal treatment.
51. The process according to any of embodiments 1 to 50, wherein the hydrothermally treated aqueous mixture is a suspension.

52. The process according to any of embodiments 1 to 50, wherein the hydrothermally treated aqueous mixture is a solution.
53. The process according to any of embodiments 1 to 52, wherein, based on the amount of water and sources of the elemental constituents present in the pressure vessel during the hydrothermal treatment, the proportion by weight of the total amount of sources is at least 1% by weight.
54. The process according to any of embodiments 1 to 53, wherein, based on the amount of water and sources of the elemental constituents present in the pressure vessel during the hydrothermal treatment, the proportion by weight of the total amount of sources is not more than 90% by weight.
55. The process according to any of embodiments 1 to 54, wherein, based on the amount of water and sources of the elemental constituents present in the pressure vessel during the hydrothermal treatment, the proportion by weight of the total amount of the sources is 3 to 60% by weight.
56. The process according to any of embodiments 1 to 55, wherein, based on the amount of water and sources of the elemental constituents present in the pressure vessel during the hydrothermal treatment, the proportion by weight of the total amount of the sources is 5 to 30% by weight.
57. The process according to any of embodiments 1 to 56, wherein, based on the amount of water and sources of the elemental constituents present in the pressure vessel during the hydrothermal treatment, the proportion by weight of the total amount of the sources is 5 to 15% by weight.
58. The process according to any of embodiments 1 to 57, wherein the aqueous mixture subjected to the hydrothermal treatment at 25° C. and 103.1 kPa has a pH of <7.
59. The process according to any of embodiments 1 to 57, wherein the aqueous mixture subjected to the hydrothermal treatment at 25° C. and 103.1 kPa has a pH of ≤6.
60. The process according to any of embodiments 1 to 57, wherein the aqueous mixture subjected to the hydrothermal treatment at 25° C. and 103.1 kPa has a pH of ≤5.
61. The process according to any of embodiments 1 to 57, wherein the aqueous mixture subjected to the hydrothermal treatment at 25° C. and 103.1 kPa has a pH of ≤4.
62. The process according to any of embodiments 1 to 57, wherein the aqueous mixture subjected to the hydrothermal treatment at 25° C. and 103.1 kPa has a pH of ≤3.
63. The process according to any of embodiments 1 to 62, wherein the aqueous mixture subjected to the hydrothermal treatment at 25° C. and 103.1 kPa has a pH of ≥0.
64. The process according to any of embodiments 1 to 63, wherein the aqueous mixture subjected to the hydrothermal treatment at 25° C. and 103.1 kPa has a pH of ≥1 and ≤3.
65. The process according to any of embodiments 1 to 64, wherein the aqueous mixture subjected to the hydrothermal treatment at 25° C. and 103.1 kPa has a pH of ≥1.5 and ≤2.5.
66. The process according to any of embodiments 58 to 65, wherein the aqueous mixture subjected to the hydrothermal treatment comprises added sulfuric acid.
67. The process according to any of embodiments 1 to 66, wherein the aqueous mixture subjected to the hydrothermal treatment is stirred during the hydrothermal treatment.
68. The process according to any of embodiments 1 to 67, wherein at least one source of the elemental constituent Mo is ammonium heptamolybdate and/or a hydrate of this compound.
69. The process according to any of embodiments 1 to 68, wherein at least one source of the elemental constituent W is ammonium paratungstate, ammonium metatungstate and/or a hydrate of these compounds.
70. The process according to any of embodiments 1 to 69, wherein at least one source of the elemental constituent vanadium comprises the vanadium in the +4 oxidation state.
71. The process according to embodiment 70, wherein at least one source of the elemental constituent vanadium is vanadyl sulfate and/or a hydrate of this compound.
72. The process according to any of embodiments 1 to 71, wherein at least one source of the elemental constituent Cu is copper(II) sulfate, copper(II) nitrate, copper(II) acetate and/or a hydrate of these compounds.
73. The process according to any of embodiments 1 to 72, wherein the hydrothermal treatment takes 0.5 h to 100 h.
74. The process according to any of embodiments 1 to 73, wherein the hydrothermal treatment takes 5 h to 80 h.
75. The process according to any of embodiments 1 to 74, wherein the hydrothermal treatment is effected in the absence or presence of molecular oxygen.
76. The process according to any of embodiments 1 to 75, wherein the removal of the solid newly forming in the course of hydrothermal treatment as the precursor composition comprises at least one mechanical removal of this solid and at least one washing operation on the mechanically removed solid with at least one wash liquid from the group consisting of organic acids, inorganic acids and aqueous solutions of the acids mentioned.
77. The process according to embodiment 76, wherein the wash liquid is an aqueous solution of oxalic acid.
78. The process according to any of embodiments 1 to 77, wherein the temperature in the course of thermal treatment of the precursor composition is 300 to 700° C.
79. The process according to any of embodiments 1 to 78, wherein the temperature in the course of thermal treatment of the precursor composition is 350 to 650° C.
80. The process according to any of embodiments 1 to 79, wherein the temperature in the course of thermal treatment of the precursor composition is 400 to 600° C.
81. The process according to any of embodiments 1 to 80, wherein the thermal treatment of the precursor composition is effected under a gas atmosphere comprising molecular oxygen.
82. The process according to any of embodiments 1 to 80, wherein the thermal treatment of the precursor composition is effected under reduced pressure or under a gas atmosphere which does not comprise any molecular oxygen.
83. The process according to any of embodiments 1 to 80, wherein the thermal treatment of the precursor composition is effected under a reducing gas atmosphere.
84. The process according to any of embodiments 81 to 83, wherein the thermal treatment of the precursor composition is effected under a gas atmosphere comprising molecular nitrogen and/or noble gas.
85. The process according to any of embodiments 1 to 80, wherein the thermal treatment of the precursor composition is effected under a gas atmosphere whose content of molecular oxygen and reducing constituents is in each case ≤3% by volume.
86. The process according to any of embodiments 1 to 85, wherein the catalytically active multimetal oxide composition in the heterogeneously catalyzed partial oxidation is in a fixed bed, a moving bed or a fluidized bed.
87. The process according to any of embodiments 1 to 86, wherein the catalytically active multimetal oxide compo- 87. ...sition is the active composition of an eggshell catalyst in which it has been applied to the surface of a support body.
88. The process according to embodiment 87, wherein the catalytically active multimetal oxide composition in the eggshell catalyst has been applied to a spherical or annular support body.
89. The process according to embodiment 88, wherein the catalytically active multimetal oxide composition has been applied to the surface of the support body using a solution of 20 to 90% by weight of water and 10 to 80% by weight of glycerol as a binder.
90. The process according to embodiment 88 or 89, wherein the longest dimension of the support body is 1 to 10 mm.
91. The process according to embodiment 88 or 89, wherein the support body is a ring whose length is 4 to 10 mm, whose external diameter is 2 to 10 mm and whose wall thickness is 1 to 4 mm.
92. The process according to embodiment 88 or 89, wherein the support body is a ring whose length is 3 to 6 mm, whose external diameter is 4 to 8 mm and whose wall thickness is 1 to 2 mm.
93. The process according to any of embodiments 87 to 92, wherein the active multimetal oxide composition in the eggshell catalyst forms an active composition shell of thickness 10 to 1000 μm.
94. The process according to any of embodiments 87 to 93, wherein the active multimetal oxide composition in the eggshell catalyst forms an active composition shell of thickness 50 to 700 μm.
95. The process according to any of embodiments 87 to 94, wherein the active multimetal oxide composition in the eggshell catalyst forms an active composition shell of thickness 100 to 600 μm.
96. The process according to any of embodiments 87 to 95, wherein the active multimetal oxide composition in the eggshell catalyst forms an active composition shell of thickness 100 to 500 μm.
97. The process according to any of embodiments 87 to 96, wherein the active multimetal oxide composition in the eggshell catalyst forms an active composition shell of thickness 150 to 300 μm.
98. The process according to any of embodiments 1 to 97, wherein the specific surface area of the active multimetal oxide composition is ≥15 m$^2$/g.
99. The process according to any of embodiments 1 to 97, wherein the specific surface area of the active multimetal oxide composition is ≥20 m$^2$/g.
100. The process according to any of embodiments 1 to 97, wherein the specific surface area of the active multimetal oxide composition is ≥25 m$^2$/g.
101. The process according to any of embodiments 1 to 97, wherein the specific surface area of the active multimetal oxide composition is ≤30 m$^2$/g.
102. The process according to any of embodiments 1 to 101, wherein the specific surface area of the active multimetal oxide composition is ≤150 m$^2$/g.
103. The process according to any of embodiments 1 to 102, wherein the specific surface area of the active multimetal oxide composition is ≤60 m$^2$/g.
104. The process according to any of embodiments 1 to 103, wherein the specific surface area of the active multimetal oxide composition is ≤40 m$^2$/g.
105. The process according to any of embodiments 1 to 104, wherein the reaction temperature in the heterogeneously catalyzed gas phase partial oxidation is in the range of 200 to 400° C.
106. The process according to any of embodiments 1 to 105, wherein the reaction temperature in the heterogeneously catalyzed gas phase partial oxidation is in the range of 220 to 380° C.
107. The process according to any of embodiments 1 to 106, wherein the reaction temperature in the heterogeneously catalyzed gas phase partial oxidation is in the range of 230 to 350° C.
108. The process according to any of embodiments 1 to 107, wherein the reaction temperature in the heterogeneously catalyzed gas phase partial oxidation is in the range of 245 to 285° C.
109. The process according to any of embodiments 1 to 108, wherein the (meth)acrolein on commencement of the gas phase partial oxidation is part of a reaction gas mixture comprising molecular oxygen, with the proviso that the molar ratio of molecular oxygen present in the reaction gas mixture to (meth)acrolein present in the reaction gas mixture is 1 to 3.
110. The process according to any of embodiments 1 to 109, wherein the (meth)acrolein on commencement of the gas phase partial oxidation is part of a reaction gas mixture also comprising steam.
111. The process according to any of embodiments 1 to 110, wherein the (meth)acrolein on commencement of the gas phase partial oxidation is part of a reaction gas mixture comprising molecular oxygen, inert gas and optionally steam, with the proviso that the (meth)acrolein:oxygen:steam:inert gas volume ratio (l(STP)) present in the reaction gas mixture is 1:(1 to 3):(0 to 20):(3 to 30).
112. The process according to any of embodiments 1 to 111, wherein the (meth)acrolein on commencement of the gas phase partial oxidation is part of a reaction gas mixture comprising molecular oxygen, inert gas and steam, with the proviso that the (meth)acrolein:oxygen:steam:inert gas volume ratio (l(STP)) present in the reaction gas mixture is 1:(1 to 3):(0.5 to 10):(7 to 10).
113. The process according to any of embodiments 1 to 112, wherein the active multimetal oxide composition has a semicrystalline structure.
114. The process according to any of embodiments 1 to 113, wherein a gas phase present in the pressure vessel during the hydrothermal treatment has a steam content of at least 30% by volume.
115. The process according to any of embodiments 1 to 113, wherein a gas phase present in the pressure vessel during the hydrothermal treatment has a steam content of at least 50% by volume.
116. The process according to any of embodiments 1 to 113, wherein a gas phase present in the pressure vessel during the hydrothermal treatment has a steam content of at least 90% by volume.
117. The process according to any of embodiments 1 to 113, wherein a gas phase present in the pressure vessel during the hydrothermal treatment has a steam content of at least 95% by volume.
118. A multimetal oxide composition of the general formula I $$Mo_{12}V_aX^1_bX^2_cX^3_dX^4_eX^5_fX^6_gO_n \qquad (I)$$

in which the variables are each defined as follows:
$X^1$=W, Nb, Ta, Cr and/or Ce,
$X^2$=Cu, Ni, Co, Fe, Mn and/or Zn,
$X^3$=Sb, Te and/or Bi,
$X^4$=one or more alkali metals (Li, Na, K, Rb and/or Cs) and/or H, $X^5$=one or more alkaline earth metals (Mg, Ca, Sr and/or Ba),
$X^6$=Si, Al, Ti and/or Zr,
a=1 to 6,
b=0.2 to 8,
c=0 to 18,
d=0 to 40,
e=0 to 4,
f=0 to 4,
g=0 to 40, and
n=a number which is determined by the valency and frequency of the elements in I other than oxygen,
where
at least 50 mol % of the total molar amount of elements $X^1$ present in the multimetal oxide composition (I) is accounted for by the element W, and
the multimetal oxide composition (I) is obtainable by a process in which a mixture of sources of the elemental constituents of the multimetal oxide composition (I) is subjected to a hydrothermal treatment in the presence of water in a pressure vessel (as an aqueous mixture), the newly forming solid is removed as a precursor composition and the precursor composition is converted to the multimetal oxide composition (I) by thermal treatment.

119. The multimetal oxide composition according to embodiment 118, wherein at least 60 mol % of the total molar amount of elements $X^1$ present in the multimetal oxide composition (I) is accounted for by the element W.

120. The multimetal oxide composition according to embodiment 118, wherein at least 70 mol % of the total molar amount of elements $X^1$ present in the multimetal oxide composition (I) is accounted for by the element W.

121. The multimetal oxide composition according to embodiment 118, wherein at least 80 mol % of the total molar amount of elements $X^1$ present in the multimetal oxide composition (I) is accounted for by the element W.

122. The multimetal oxide composition according to embodiment 118, wherein at least 90 mol % of the total molar amount of elements $X^1$ present in the multimetal oxide composition (I) is accounted for by the element W.

123. The multimetal oxide composition according to embodiment 118, wherein at least 95 mol % of the total molar amount of elements $X^1$ present in the multimetal oxide composition (I) is accounted for by the element W.

124. The multimetal oxide composition according to embodiment 118, wherein 100 mol % of the total molar amount of elements $X^1$ present in the multimetal oxide composition (I) is accounted for by the element W.

125. The multimetal oxide composition according to any of embodiments 118 to 124, wherein the stoichiometric coefficient b is 0.2 to 4.

126. The multimetal oxide composition according to any of embodiments 118 to 124, wherein the stoichiometric coefficient b is 0.2 to 3.

127. The multimetal oxide composition according to any of embodiments 118 to 126, wherein the stoichiometric coefficient c is 0.5 to 18.

128. The multimetal oxide composition according to any of embodiments 118 to 127, wherein the stoichiometric coefficient c is 0.5 to 10.

129. The multimetal oxide composition according to any of embodiments 118 to 128, wherein the stoichiometric coefficient c is 0.5 to 3.

130. The multimetal oxide composition according to any of embodiments 118 to 129, wherein the stoichiometric coefficient a is 1 to 5.

131. The multimetal oxide composition according to any of embodiments 118 to 130, wherein the stoichiometric coefficient a is 2 to 4.

132. The multimetal oxide composition according to any of embodiments 118 to 131, wherein the stoichiometric coefficient d is 0 to 20.

133. The multimetal oxide composition according to any of embodiments 118 to 132, wherein the stoichiometric coefficient d is 0 to 10.

134. The multimetal oxide composition according to any of embodiments 118 to 133, wherein the stoichiometric coefficient d is 0 to 2.

135. The multimetal oxide composition according to any of embodiments 118 to 134, wherein the stoichiometric coefficient e is 0 to 2.

136. The multimetal oxide composition according to any of embodiments 118 to 135, wherein the stoichiometric coefficient f is 0 to 2.

137. The multimetal oxide composition according to any of embodiments 118 to 136, wherein $X^1$=W, Nb and/or Cr.

138. The multimetal oxide composition according to any of embodiments 118 to 136, wherein $X^1$=W and Nb.

139. The multimetal oxide composition according to any of embodiments 118 to 136, wherein $X^1$=W.

140. The multimetal oxide composition according to any of embodiments 118 to 139, wherein $X^2$=Cu, Ni, Co and/or Fe.

141. The multimetal oxide composition according to any of embodiments 118 to 139, wherein $X^2$=Cu and/or Ni.

142. The multimetal oxide composition according to any of embodiments 118 to 139, wherein $X^2$=Cu.

143. The multimetal oxide composition according to any of embodiments 118 to 142, wherein $X^3$=Sb.

144. The multimetal oxide composition according to any of embodiments 118 to 143, wherein $X^4$=Na, K and/or H.

145. The multimetal oxide composition according to any of embodiments 118 to 144, wherein $X^5$=Ca, Sr and/or Ba.

146. The multimetal oxide composition according to any of embodiments 118 to 145, wherein $X^6$=Si, Al and/or Ti.

147. The multimetal oxide composition according to any of embodiments 118 to 145, wherein $X^6$=Si and/or Al.

148. The multimetal oxide composition according to any of embodiments 118 to 124, wherein the variables of the general formula I are each defined as follows:
$X^1$=W, Nb and/or Cr,
$X^2$=Cu, Ni, Co and/or Fe
$X^3$=Sb,
$X^4$=Na, K and/or H,
$X^5$=Ca, Sr and/or Ba,
$X^6$=Si, Al and/or Ti,
a=1 to 5,
b=0.2 to 4,
c=0.5 to 18,
d=0 to 10,
e=0 to 2,
f=0 to 2,
g=0 to 15, and
n=a number which is determined by the valency and frequency of the elements in the general formula I other than oxygen.

149. The multimetal oxide composition according to embodiment 148, wherein at least 50 mol % of the total molar amount of elements $X^2$ present in the multimetal oxide composition (I) is accounted for by the element Cu.

150. The multimetal oxide composition according to embodiment 148, wherein at least 70 mol % of the total molar amount of elements $X^2$ present in the multimetal oxide composition (I) is accounted for by the element Cu.
151. The multimetal oxide composition according to embodiment 148, wherein at least 90 mol % of the total molar amount of elements $X^2$ present in the multimetal oxide composition (I) is accounted for by the element Cu.
152. The multimetal oxide composition according to embodiment 148, wherein 100 mol % of the total molar amount of elements $X^2$ present in the multimetal oxide composition (I) is accounted for by the element Cu.
153. The multimetal oxide composition according to any of embodiments 118 to 124, wherein the catalytically active multimetal oxide composition satisfies the general stoichiometry II $$Mo_{12}V_aX^1_bX^2_cX^4_eX^5_fX^6_gO_n \quad (II)$$

in which the variables are each defined as follows:
$X^1$=W and/or Nb,
$X^2$=Cu and/or Ni,
$X^4$=H,
$X^5$=Ca and/or Sr,
$X^6$=Si and/or Al,
a=2 to 4,
b=0.2 to 3,
c=0.5 to 3,
e=0 to 2,
f=0 to 0.5,
g=0 to 8, and
n=a number which is determined by the valency and frequency of the elements in the general formula II other than oxygen.
154. The multimetal oxide composition according to embodiment 153, wherein at least 50 mol % of the total molar amount of elements $X^2$ present in the multimetal oxide composition is accounted for by the element Cu.
155. The multimetal oxide composition according to embodiment 153, wherein at least 70 mol % of the total molar amount of elements $X^2$ present in the multimetal oxide composition is accounted for by the element Cu.
156. The multimetal oxide composition according to embodiment 153, wherein at least 90 mol % of the total molar amount of elements $X^2$ present in the multimetal oxide composition is accounted for by the element Cu.
157. The multimetal oxide composition according to embodiment 153, wherein 100 mol % of the total molar amount of elements $X^2$ present in the multimetal oxide composition is accounted for by the element Cu.
158. The multimetal oxide composition according to any of embodiments 118 to 124, wherein the catalytically active multimetal oxide composition satisfies the general stoichiometry III $$Mo_{12}V_aW_bCu_cX^4_eX^5_fX^6_gO_n \quad (III)$$

in which the variables are each defined as follows:
$X^4$=one or more alkali metals (Li, Na, K, Rb and/or Cs) and/or H,
$X^5$=one or more alkaline earth metals (Mg, Ca, Sr and/or Ba),
$X^6$=one or more elements from the group of Si, Al, Ti and Zr,
a=2 to 4,
b=0.2 to 3,
c=0.5 to 2,
e=0 to 4,
f=0 to 4, with the proviso that the sum of e and f does not exceed 4,
g=0 to 40, and
n=a number which is determined by the valency and frequency of the elements in the general formula III other than oxygen.
159. The multimetal oxide composition according to embodiment 158, wherein the stoichiometric coefficient b is 0.5 to 2.
160. The multimetal oxide composition according to embodiment 158 or 159, wherein the stoichiometric coefficient a is 2.5 to 3.5.
161. The multimetal oxide composition according to any of embodiments 158 to 160, wherein the stoichiometric coefficient c is 1 to 1.5.
162. The multimetal oxide composition according to any of embodiments 118 to 161, wherein the hydrothermal treatment is effected at temperatures in the range of >100° C. to 600° C.
163. The multimetal oxide composition according to any of embodiments 118 to 162, wherein the hydrothermal treatment is effected at temperatures in the range of ≥110° C. to 400° C.
164. The multimetal oxide composition according to any of embodiments 118 to 163, wherein the hydrothermal treatment is effected at temperatures in the range of ≥130° C. to 300° C.
165. The multimetal oxide composition according to any of embodiments 118 to 164, wherein the hydrothermal treatment is effected at a superatmospheric working pressure of ≤50 MPa.
166. The multimetal oxide composition according to any of embodiments 118 to 165, wherein the hydrothermal treatment is effected at a working pressure of ≥200 kPa and ≤25 MPa or at a working pressure of ≥500 kPa and ≤22 MPa.
167. The multimetal oxide composition according to any of embodiments 118 to 166, wherein steam and liquid water coexist during the hydrothermal treatment.
168. The multimetal oxide composition according to any of embodiments 118 to 167, wherein the hydrothermally treated aqueous mixture is a suspension.
169. The multimetal oxide composition according to any of embodiments 118 to 167, wherein the hydrothermally treated aqueous mixture is a solution.
170. The multimetal oxide composition according to any of embodiments 118 to 169, wherein, based on the amount of water and sources of the elemental constituents present in the pressure vessel during the hydrothermal treatment, the proportion by weight of the total amount of sources is at least 1% by weight.
171. The multimetal oxide composition according to any of embodiments 118 to 170, wherein, based on the amount of water and sources of the elemental constituents present in the pressure vessel during the hydrothermal treatment, the proportion by weight of the total amount of sources is not more than 90% by weight.
172. The multimetal oxide composition according to any of embodiments 118 to 171, wherein, based on the amount of water and sources of the elemental constituents present in the pressure vessel during the hydrothermal treatment, the proportion by weight of the total amount of the sources is 3 to 60% by weight.
173. The multimetal oxide composition according to any of embodiments 118 to 172, wherein, based on the amount of water and sources of the elemental constituents present in the pressure vessel during the hydrothermal treatment, the proportion by weight of the total amount of the sources is 5 to 30% by weight.
174. The multimetal oxide composition according to any of embodiments 118 to 173, wherein, based on the amount of water and sources of the elemental constituents present in the pressure vessel during the hydrothermal treatment, the proportion by weight of the total amount of the sources is 5 to 15% by weight.

175. The multimetal oxide composition according to any of embodiments 118 to 174, wherein the aqueous mixture subjected to the hydrothermal treatment at 25° C. and 103.1 kPa has a pH of <7.

176. The multimetal oxide composition according to any of embodiments 118 to 174, wherein the aqueous mixture subjected to the hydrothermal treatment at 25° C. and 103.1 kPa has a pH of ≤6.

177. The multimetal oxide composition according to any of embodiments 118 to 174, wherein the aqueous mixture subjected to the hydrothermal treatment at 25° C. and 103.1 kPa has a pH of ≤5.

178. The multimetal oxide composition according to any of embodiments 118 to 174, wherein the aqueous mixture subjected to the hydrothermal treatment at 25° C. and 103.1 kPa has a pH of ≤4.

179. The multimetal oxide composition according to any of embodiments 118 to 174, wherein the aqueous mixture subjected to the hydrothermal treatment at 25° C. and 103.1 kPa has a pH of ≤3.

180. The multimetal oxide composition according to any of embodiments 118 to 179, wherein the aqueous mixture subjected to the hydrothermal treatment at 25° C. and 103.1 kPa has a pH of ≥0.

181. The multimetal oxide composition according to any of embodiments 118 to 180, wherein the aqueous mixture subjected to the hydrothermal treatment at 25° C. and 103.1 kPa has a pH of ≥1 and ≤3.

182. The multimetal oxide composition according to any of embodiments 118 to 181, wherein the aqueous mixture subjected to the hydrothermal treatment at 25° C. and 103.1 kPa has a pH of ≥1.5 and ≤2.5.

183. The multimetal oxide composition according to any of embodiments 175 to 182, wherein the aqueous mixture subjected to the hydrothermal treatment comprises added sulfuric acid.

184. The multimetal oxide composition according to any of embodiments 118 to 183, wherein the aqueous mixture subjected to the hydrothermal treatment is stirred during the hydrothermal treatment.

185. The multimetal oxide composition according to any of embodiments 118 to 184, wherein at least one source of the elemental constituent Mo is ammonium heptamolybdate and/or a hydrate of this compound.

186. The multimetal oxide composition according to any of embodiments 118 to 185, wherein at least one source of the elemental constituent W is ammonium paratungstate, ammonium metatungstate and/or a hydrate of these compounds.

187. The multimetal oxide composition according to any of embodiments 118 to 186, wherein at least one source of the elemental constituent vanadium comprises the vanadium in the +4 oxidation state.

188. The multimetal oxide composition according to embodiment 187, wherein at least one source of the elemental constituent vanadium is vanadyl sulfate and/or a hydrate of this compound.

189. The multimetal oxide composition according to any of embodiments 118 to 188, wherein at least one source of the elemental constituent Cu is copper(II) sulfate, copper(II) nitrate, copper(II) acetate and/or a hydrate of these compounds.

190. The multimetal oxide composition according to any of embodiments 118 to 189, wherein the hydrothermal treatment takes 0.5 h to 100 h.

191. The multimetal oxide composition according to any of embodiments 118 to 190, wherein the hydrothermal treatment takes 5 h to 80 h.

192. The multimetal oxide composition according to any of embodiments 118 to 191, wherein the hydrothermal treatment is effected in the absence or presence of molecular oxygen.

193. The multimetal oxide composition according to any of embodiments 118 to 192, wherein the removal of the solid newly forming in the course of hydrothermal treatment as the precursor composition comprises at least one mechanical removal of this solid and at least one washing operation on the mechanically removed solid with at least one wash liquid from the group consisting of organic acids, inorganic acids and aqueous solutions of the acids mentioned.

194. The multimetal oxide composition according to embodiment 193, wherein the wash liquid is an aqueous solution of oxalic acid.

195. The multimetal oxide composition according to any of embodiments 118 to 194, wherein the temperature in the course of thermal treatment of the precursor composition is 300 to 700° C.

196. The multimetal oxide composition according to any of embodiments 118 to 195, wherein the temperature in the course of thermal treatment of the precursor composition is 350 to 650° C.

197. The multimetal oxide composition according to any of embodiments 118 to 196, wherein the temperature in the course of thermal treatment of the precursor composition is 400 to 600° C.

198. The multimetal oxide composition according to any of embodiments 118 to 197, wherein the thermal treatment of the precursor composition is effected under a gas atmosphere comprising molecular oxygen.

199. The multimetal oxide composition according to any of embodiments 118 to 197, wherein the thermal treatment of the precursor composition is effected under reduced pressure or under a gas atmosphere which does not comprise any molecular oxygen.

200. The multimetal oxide composition according to any of embodiments 118 to 197, wherein the thermal treatment of the precursor composition is effected under a reducing gas atmosphere.

201. The multimetal oxide composition according to any of embodiments 198 to 200, wherein the thermal treatment of the precursor composition is effected under a gas atmosphere comprising molecular nitrogen and/or noble gas.

202. The multimetal oxide composition according to any of embodiments 118 to 197, wherein the thermal treatment of the precursor composition is effected under a gas atmosphere whose content of molecular oxygen and reducing constituents is in each case ≤3% by volume.

203. The multimetal oxide composition according to any of embodiments 118 to 202, wherein the specific surface area of the multimetal oxide composition is ≥15 m²/g.

204. The multimetal oxide composition according to any of embodiments 118 to 202, wherein the specific surface area of the multimetal oxide composition is ≥20 m²/g.

205. The multimetal oxide composition according to any of embodiments 118 to 202, wherein the specific surface area of the multimetal oxide composition is ≥25 m²/g.

206. The multimetal oxide composition according to any of embodiments 118 to 202, wherein the specific surface area of the multimetal oxide composition is ≥30 m²/g.

207. The multimetal oxide composition according to any of embodiments 118 to 206, wherein the specific surface area of the multimetal oxide composition is ≤150 m²/g.
208. The multimetal oxide composition according to any of embodiments 118 to 207, wherein the specific surface area of the multimetal oxide composition is ≤60 m²/g.
209. The multimetal oxide composition according to any of embodiments 118 to 208, wherein the specific surface area of the multimetal oxide composition is ≤40 m²/g.
210. The multimetal oxide composition according to any of embodiments 118 to 209, which has a semicrystalline structure.
211. The multimetal oxide composition according to any of embodiments 118 to 210, wherein a gas phase present in the pressure vessel during the hydrothermal treatment has a steam content of at least 30% by volume.
212. The multimetal oxide composition according to any of embodiments 118 to 210, wherein a gas phase present in the pressure vessel during the hydrothermal treatment has a steam content of at least 50% by volume.
213. The multimetal oxide composition according to any of embodiments 118 to 210, wherein a gas phase present in the pressure vessel during the hydrothermal treatment has a steam content of at least 90% by volume.
214. The multimetal oxide composition according to any of embodiments 118 to 210, wherein a gas phase present in the pressure vessel during the hydrothermal treatment has a steam content of at least 95% by volume.
215. The use of a multimetal oxide composition according to any of embodiments 118 to 214 as a catalytic active composition for the performance of a heterogeneously catalyzed gas phase partial oxidation of (meth)acrolein to (meth)acrylic acid.
216. An eggshell catalyst consisting of a support body and a catalytic active composition applied to the surface of the support body, and optionally binders for application of the active composition to the surface of the support body, wherein the catalytic active composition is a multimetal oxide composition according to any of embodiments 118 to 214.
217. The eggshell catalyst according to embodiment 216, wherein the multimetal oxide composition in the eggshell catalyst has been applied to a spherical or annular support body.
218. The eggshell catalyst according to embodiment 216 or 217, wherein the multimetal oxide composition has been applied to the support body with a solution composed of 20 to 90% by weight of water and 10 to 80% by weight of glycerol as a binder.
219. The eggshell catalyst according to any of embodiments 216 to 218, wherein the longest dimension of the support body is 1 to 10 mm.
220. The eggshell catalyst according to any of embodiments 216 to 219, wherein the support body is a ring whose length is 4 to 10 mm, whose external diameter is 2 to 10 mm and whose wall thickness is 1 to 4 mm.
221. The eggshell catalyst according to embodiment 216 or 219, wherein the support body is a ring whose length is 3 to 6 mm, whose external diameter is 4 to 8 mm and whose wall thickness is 1 to 2 mm.
222. The eggshell catalyst according to any of embodiments 216 to 221, wherein the multimetal oxide composition in the eggshell catalyst forms an active composition shell of thickness 10 to 1000 μm.
223. The eggshell catalyst according to any of embodiments 216 to 222, wherein the multimetal oxide composition in the eggshell catalyst forms an active composition shell of thickness 50 to 700 μm.
224. The eggshell catalyst according to any of embodiments 216 to 223, wherein the multimetal oxide composition in the eggshell catalyst forms an active composition shell of thickness 100 to 600 μm.
225. The eggshell catalyst according to any of embodiments 216 to 224, wherein the multimetal oxide composition in the eggshell catalyst forms an active composition shell of thickness 100 to 500 μm.
226. The eggshell catalyst according to any of embodiments 216 to 225, wherein the active multimetal oxide composition in the eggshell catalyst forms an active composition shell of thickness 150 to 300 μm.
227. The use of an eggshell catalyst according to any of embodiments 216 to 226 as a catalyst for the performance of a heterogeneously catalyzed gas phase partial oxidation of (meth)acrolein to (meth)acrylic acid.
228. A process for preparing a multimetal oxide composition of the general formula I $$Mo_{12}V_aX^1_bX^2_cX^3_dX^4_eX^5_fX^6_gO_n \qquad (I)$$

in which the variables are each defined as follows:
$X^1$=W, Nb, Ta, Cr and/or Ce,
$X^2$=Cu, Ni, Co, Fe, Mn and/or Zn,
$X^3$=Sb, Te and/or Bi,
$X^4$=one or more alkali metals (Li, Na, K, Rb and/or Cs) and/or H,
$X^5$=one or more alkaline earth metals (Mg, Ca, Sr and/or Ba),
$X^6$=Si, Al, Ti and/or Zr,
a=1 to 6,
b=0.2 to 8,
c=0 to 18,
d=0 to 40,
e=0 to 4,
f=0 to 4,
g=0 to 40, and
n=a number which is determined by the valency and frequency of the elements in I other than oxygen,
wherein
at least 50 mol % of the total molar amount of elements $X^1$ present in the multimetal oxide composition (I) is accounted for by the element W, and
the multimetal oxide composition (I) is obtained by subjecting a mixture of sources of the elemental constituents of the multimetal oxide composition (I) to a hydrothermal treatment in the presence of water in a pressure vessel (as an aqueous mixture), removing the newly forming solid as a precursor composition and converting the precursor composition to the multimetal oxide composition (I) by thermal treatment.
228. The process according to embodiment 227, wherein at least 60 mol % of the total molar amount of elements $X^1$ present in the multimetal oxide composition (I) is accounted for by the element W.
229. The process according to embodiment 227, wherein at least 70 mol % of the total molar amount of elements $X^1$ present in the multimetal oxide composition (I) is accounted for by the element W.
230. The process according to embodiment 227, wherein at least 80 mol % of the total molar amount of elements $X^1$ present in the multimetal oxide composition (I) is accounted for by the element W.

231. The process according to embodiment 227, wherein at least 90 mol % of the total molar amount of elements $X^1$ present in the multimetal oxide composition (I) is accounted for by the element W.

232. The process according to embodiment 227, wherein at least 95 mol % of the total molar amount of elements $X^1$ present in the multimetal oxide composition (I) is accounted for by the element W.

233. The process according to embodiment 227, wherein 100 mol % of the total molar amount of elements $X^1$ present in the multimetal oxide composition (I) is accounted for by the element W.

234. The process according to any of embodiments 227 to 233, wherein the stoichiometric coefficient b is 0.2 to 4.

235. The process according to any of embodiments 227 to 233, wherein the stoichiometric coefficient b is 0.2 to 3.

236. The process according to any of embodiments 227 to 235, wherein the stoichiometric coefficient c is 0.5 to 18.

237. The process according to any of embodiments 227 to 235, wherein the stoichiometric coefficient c is 0.5 to 10.

238. The process according to any of embodiments 227 to 235, wherein the stoichiometric coefficient c is 0.5 to 3.

239. The process according to any of embodiments 227 to 238, wherein the stoichiometric coefficient a is 1 to 5.

240. The process according to any of embodiments 227 to 239, wherein the stoichiometric coefficient a is 2 to 4.

241. The process according to any of embodiments 227 to 240, wherein the stoichiometric coefficient d is 0 to 20.

242. The process according to any of embodiments 227 to 240, wherein the stoichiometric coefficient d is 0 to 10.

243. The process according to any of embodiments 227 to 240, wherein the stoichiometric coefficient d is 0 to 2.

244. The process according to any of embodiments 227 to 240, wherein the stoichiometric coefficient e is 0 to 2.

245. The process according to any of embodiments 227 to 244, wherein the stoichiometric coefficient f is 0 to 2.

246. The process according to any of embodiments 227 to 245, wherein $X^1$=W, Nb and/or Cr.

247. The process according to any of embodiments 227 to 245, wherein $X^1$=W and Nb.

248. The process according to any of embodiments 227 to 245, wherein $X^1$=W.

249. The process according to any of embodiments 227 to 248, wherein $X^2$=Cu, Ni, Co and/or Fe.

250. The process according to any of embodiments 227 to 248, wherein $X^2$=Cu and/or Ni.

251. The process according to any of embodiments 227 to 248, wherein $X^2$=Cu.

252. The process according to any of embodiments 227 to 251, wherein $X^3$=Sb.

253. The process according to any of embodiments 227 to 252, wherein $X^4$=Na, K and/or H.

254. The process according to any of embodiments 227 to 253, wherein $X^5$=Ca, Sr and/or Ba.

255. The process according to any of embodiments 227 to 254, wherein $X^6$=Si, Al and/or Ti.

256. The process according to any of embodiments 227 to 254, wherein $X^6$=Si and/or Al.

257. The process according to any of embodiments 227 to 233, wherein the variables of the general formula I are each defined as follows:
$X^1$=W, Nb and/or Cr,
$X^2$=Cu, Ni, Co and/or Fe
$X^3$=Sb,
$X^4$=Na, K and/or H,
$X^5$=Ca, Sr and/or Ba,
$X^6$=Si, Al and/or Ti,
a=1 to 5,
b=0.2 to 4,
c=0.5 to 18,
d=0 to 10,
e=0 to 2,
f=0 to 2,
g=0 to 15, and
n=a number which is determined by the valency and frequency of the elements in the general formula I other than oxygen.

258. The process according to embodiment 257, wherein at least 50 mol % of the total molar amount of elements $X^2$ present in the multimetal oxide composition (I) is accounted for by the element Cu.

259. The process according to embodiment 257, wherein at least 70 mol % of the total molar amount of elements $X^2$ present in the multimetal oxide composition (I) is accounted for by the element Cu.

260. The process according to embodiment 257, wherein at least 90 mol % of the total molar amount of elements $X^2$ present in the multimetal oxide composition (I) is accounted for by the element Cu.

261. The process according to embodiment 257, wherein 100 mol % of the total molar amount of elements $X^2$ present in the multimetal oxide composition (I) is accounted for by the element Cu.

262. The process according to any of embodiments 227 to 233, wherein the catalytically active multimetal oxide composition satisfies the general stoichiometry II $$Mo_{12}V_aX^1_bX^2_cX^4_eX^5_fX^6_gO_n \quad (II)$$

in which the variables are each defined as follows:
$X^1$=W and/or Nb,
$X^2$=Cu and/or Ni,
$X^4$=H,
$X^5$=Ca and/or Sr,
$X^6$=Si and/or Al,
a=2 to 4,
b=0.2 to 3,
c=0.5 to 3,
e=0 to 2,
f=0 to 0.5,
g=0 to 8, and
n=a number which is determined by the valency and frequency of the elements in the general formula II other than oxygen.

263. The process according to embodiment 262, wherein at least 50 mol % of the total molar amount of elements $X^2$ present in the multimetal oxide composition is accounted for by the element Cu.

264. The process according to embodiment 262, wherein at least 70 mol % of the total molar amount of elements $X^2$ present in the multimetal oxide composition is accounted for by the element Cu.

265. The process according to embodiment 262, wherein at least 90 mol % of the total molar amount of elements $X^2$ present in the multimetal oxide composition is accounted for by the element Cu.

266. The process according to embodiment 262, wherein 100 mol % of the total molar amount of elements $X^2$ present in the multimetal oxide composition is accounted for by the element Cu.

267. The process according to any of embodiments 227 to 233, wherein the catalytically active multimetal oxide composition satisfies the general stoichiometry III $$Mo_{12}V_aW_bCu_cX^4_eX^5_fX^6_gO_n \quad (III)$$

in which the variables are each defined as follows:
$X^4$=one or more alkali metals (Li, Na, K, Rb and/or Cs) and/or H,
$X^5$=one or more alkaline earth metals (Mg, Ca, Sr and/or Ba),
$X^6$=one or more elements from the group of Si, Al, Ti and Zr,
a=2 to 4,
b=0.2 to 3,
c=0.5 to 2,
e=0 to 4,
f=0 to 4, with the proviso that the sum of e and f does not exceed 4,
g=0 to 40, and
n=a number which is determined by the valency and frequency of the elements in the general formula III other than oxygen.

268. The process according to embodiment 267, wherein the stoichiometric coefficient b is 0.5 to 2.

269. The process according to embodiment 267 or 268, wherein the stoichiometric coefficient a is 2.5 to 3.5.

270. The process according to any of embodiments 267 to 269, wherein the stoichiometric coefficient c is 1 to 1.5.

271. The process according to any of embodiments 227 to 270, wherein the hydrothermal treatment is effected at temperatures in the range of >100° C. to 600° C.

272. The process according to any of embodiments 227 to 271, wherein the hydrothermal treatment is effected at temperatures in the range of ≥110° C. to 400° C.

273. The process according to any of embodiments 227 to 272, wherein the hydrothermal treatment is effected at temperatures in the range of ≥130° C. to 300° C.

274. The process according to any of embodiments 227 to 273, wherein the hydrothermal treatment is effected at a superatmospheric working pressure of ≤50 MPa.

275. The process according to any of embodiments 227 to 274, wherein the hydrothermal treatment is effected at a working pressure of ≥200 kPa and ≤25 MPa or at a working pressure of ≥500 kPa and ≤22 MPa.

276. The process according to any of embodiments 227 to 275, wherein steam and liquid water coexist during the hydrothermal treatment.

277. The process according to any of embodiments 227 to 276, wherein the hydrothermally treated aqueous mixture is a suspension.

278. The process according to any of embodiments 227 to 276, wherein the hydrothermally treated aqueous mixture is a solution.

279. The process according to any of embodiments 227 to 278, wherein, based on the amount of water and sources of the elemental constituents present in the pressure vessel during the hydrothermal treatment, the proportion by weight of the total amount of sources is at least 1% by weight.

280. The process according to any of embodiments 227 to 279, wherein, based on the amount of water and sources of the elemental constituents present in the pressure vessel during the hydrothermal treatment, the proportion by weight of the total amount of sources is not more than 90% by weight.

281. The process according to any of embodiments 227 to 280, wherein, based on the amount of water and sources of the elemental constituents present in the pressure vessel during the hydrothermal treatment, the proportion by weight of the total amount of the sources is 3 to 60% by weight.

282. The process according to any of embodiments 227 to 280, wherein, based on the amount of water and sources of the elemental constituents present in the pressure vessel during the hydrothermal treatment, the proportion by weight of the total amount of the sources is 5 to 30% by weight.

283. The process according to any of embodiments 227 to 282, wherein, based on the amount of water and sources of the elemental constituents present in the pressure vessel during the hydrothermal treatment, the proportion by weight of the total amount of the sources is 5 to 15% by weight.

284. The process according to any of embodiments 227 to 283, wherein the aqueous mixture subjected to the hydrothermal treatment at 25° C. and 103.1 kPa has a pH of <7.

285. The process according to any of embodiments 227 to 283, wherein the aqueous mixture subjected to the hydrothermal treatment at 25° C. and 103.1 kPa has a pH of ≤6.

286. The process according to any of embodiments 227 to 283, wherein the aqueous mixture subjected to the hydrothermal treatment at 25° C. and 103.1 kPa has a pH of ≤5.

287. The process according to any of embodiments 227 to 283, wherein the aqueous mixture subjected to the hydrothermal treatment at 25° C. and 103.1 kPa has a pH of ≤4.

288. The process according to any of embodiments 227 to 283, wherein the aqueous mixture subjected to the hydrothermal treatment at 25° C. and 103.1 kPa has a pH of ≤3.

289. The process according to any of embodiments 227 to 288, wherein the aqueous mixture subjected to the hydrothermal treatment at 25° C. and 103.1 kPa has a pH of ≥0.

290. The process according to any of embodiments 227 to 289, wherein the aqueous mixture subjected to the hydrothermal treatment at 25° C. and 103.1 kPa has a pH of ≥1 and ≤3.

291. The process according to any of embodiments 227 to 290, wherein the aqueous mixture subjected to the hydrothermal treatment at 25° C. and 103.1 kPa has a pH of ≥1.5 and ≤2.5.

292. The process according to any of embodiments 227 to 291, wherein the aqueous mixture subjected to the hydrothermal treatment comprises added sulfuric acid.

293. The process according to any of embodiments 227 to 292, wherein the aqueous mixture subjected to the hydrothermal treatment is stirred during the hydrothermal treatment.

294. The process according to any of embodiments 227 to 293, wherein at least one source of the elemental constituent Mo is ammonium heptamolybdate and/or a hydrate of this compound.

295. The process according to any of embodiments 227 to 294, wherein at least one source of the elemental constituent W is ammonium paratungstate, ammonium metatungstate and/or a hydrate of these compounds.

296. The process according to any of embodiments 227 to 295, wherein at least one source of the elemental constituent vanadium comprises the vanadium in the +4 oxidation state.

297. The process according to embodiment 296, wherein at least one source of the elemental constituent vanadium is vanadyl sulfate and/or a hydrate of this compound.

298. The process according to any of embodiments 227 to 297, wherein at least one source of the elemental constituent Cu is copper(II) sulfate, copper(II) nitrate, copper(II) acetate and/or a hydrate of these compounds.

299. The process according to any of embodiments 227 to 298, wherein the hydrothermal treatment takes 0.5 h to 100 h.

300. The process according to any of embodiments 227 to 299, wherein the hydrothermal treatment takes 5 h to 80 h.
301. The process according to any of embodiments 227 to 300, wherein the hydrothermal treatment is effected in the absence or presence of molecular oxygen.
302. The process according to any of embodiments 227 to 301, wherein the removal of the solid newly formed in the course of hydrothermal treatment as the precursor composition comprises at least one mechanical removal of this solid and at least one washing operation on the mechanically removed solid with at least one wash liquid from the group consisting of organic acids, inorganic acids and aqueous solutions of the acids mentioned.
303. The process according to embodiment 302, wherein the wash liquid is an aqueous solution of oxalic acid.
304. The process according to any of embodiments 227 to 303, wherein the temperature in the course of thermal treatment of the precursor composition is 300 to 700° C.
305. The process according to any of embodiments 227 to 304, wherein the temperature in the course of thermal treatment of the precursor composition is 350 to 650° C.
306. The process according to any of embodiments 227 to 305, wherein the temperature in the course of thermal treatment of the precursor composition is 400 to 600° C.
307. The process according to any of embodiments 227 to 306, wherein the thermal treatment of the precursor composition is effected under a gas atmosphere comprising molecular oxygen.
308. The process according to any of embodiments 227 to 306, wherein the thermal treatment of the precursor composition is effected under reduced pressure or under a gas atmosphere which does not comprise any molecular oxygen.
309. The process according to any of embodiments 227 to 306, wherein the thermal treatment of the precursor composition is effected under a reducing gas atmosphere.
310. The process according to any of embodiments 307 to 309, wherein the thermal treatment of the precursor composition is effected under a gas atmosphere comprising molecular nitrogen and/or noble gas.
311. The process according to any of embodiments 227 to 306, wherein the thermal treatment of the precursor composition is effected under a gas atmosphere whose content of molecular oxygen and reducing constituents is in each case ≤3% by volume.
312. The process according to any of embodiments 227 to 311, wherein a gas phase present in the pressure vessel during the hydrothermal treatment has a steam content of at least 30% by volume.
313. The process according to any of embodiments 227 to 311, wherein a gas phase present in the pressure vessel during the hydrothermal treatment has a steam content of at least 50% by volume.
314. The process according to any of embodiments 227 to 311, wherein a gas phase present in the pressure vessel during the hydrothermal treatment has a steam content of at least 90% by volume.
315. The process according to any of embodiments 227 to 311, wherein a gas phase present in the pressure vessel during the hydrothermal treatment has a steam content of at least 95% by volume.
316. A process for producing an eggshell catalyst by applying a finely divided multimetal oxide to the surface of a support body with the aid of a liquid binder, wherein the finely divided multimetal oxide is a multimetal oxide composition according to any of embodiments 118 to 214.
317. The process according to embodiment 316, wherein the support body is spherical or annular.
318. The process according to embodiment 316 or 317, wherein the liquid binder is a solution composed of 20 to 90% by weight of water and 10 to 80% by weight of glycerol.
319. The process according to any of embodiments 316 to 318, wherein the longest dimension of the support body is 1 to 10 mm.
320. The process according to any of embodiments 316 to 319, wherein the support body is a ring whose length is 4 to 10 mm, whose external diameter is 2 to 10 mm and whose wall thickness is 1 to 4 mm.
321. The process according to either of embodiments 316 and 319, wherein the support body is a ring whose length is 3 to 6 mm, whose external diameter is 4 to 8 mm and whose wall thickness is 1 to 2 mm.
322. The process according to any of embodiments 316 to 321, wherein the multimetal oxide composition is applied to the surface of the support body as an active composition shell of thickness 10 to 1000 μm.
323. The process according to any of embodiments 316 to 322, wherein the multimetal oxide composition is applied to the surface of the support body as an active composition shell of thickness 50 to 700 μm.
324. The process according to any of embodiments 316 to 323, wherein the multimetal oxide composition is applied to the surface of the support body as an active composition shell of thickness 100 to 600 μm.
325. The process according to any of embodiments 316 to 324, wherein the multimetal oxide composition is applied to the surface of the support body as an active composition shell of thickness 100 to 500 μm.
326. The process according to any of embodiments 316 to 325, wherein the multimetal oxide composition is applied to the surface of the support body as an active composition shell of thickness 150 to 300 μm.
327. A process for heterogeneously catalyzed gas phase partial oxidation of (meth)acrolein to (meth)acrylic acid over a catalytically active multimetal oxide composition, wherein the multimetal oxide composition is a multimetal oxide composition according to any of embodiments 118 to 214.
328. A process for heterogeneously catalyzed gas phase partial oxidation of (meth)acrolein to (meth)acrylic acid over an eggshell catalyst, wherein the eggshell catalyst is an eggshell catalyst according to any of embodiments 316 to 326.

U.S. Provisional Patent Application No. 61/645082, filed May 10, 2012, is incorporated into the present patent application by literature reference.

With regard to the above mentioned teachings, numerous changes and deviations from the present invention are possible. It can therefore be assumed that the invention, within the scope of the appended claims, can be performed differently than the way described specifically herein.

EXAMPLES AND COMPARATIVE EXAMPLES

Figure 1:
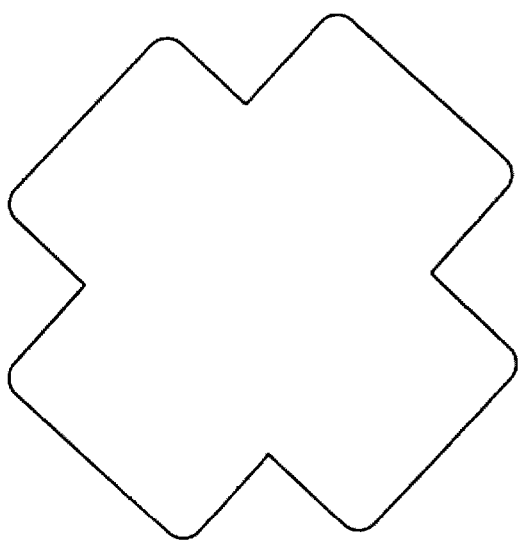
FIG. 1 shows the cross section of an inner tube.

1. Hydrothermal preparation of a comparative mixed oxide of the stoichiometry $Mo_{12}V_4O_x$ and analysis of the performance thereof in long-term operation of a partial oxidation of acrolein to acrylic acid heterogeneously catalyzed thereby a) Preparation of the aqueous mixture for hydrothermal treatment First of all, 8.83 g (=50 mmol of Mo) of ammonium heptamolybdate tetrahydrate $[(NH_4)_6Mo_7O_{24}\cdot 4H_2O]$ were dissolved in 120 ml of water at 25° C. Once the resulting yellow solution had been stirred thereafter at 25° C. for a further 30 minutes, it formed a first aqueous solution. Dissolution of 3.28 g of a vanadyl sulfate hydrate (=12.5 mmol of V) in 120 ml of water at 25° C. produced a second aqueous solution. While constantly stirring the first aqueous solution with maintenance of the 25° C., the second aqueous solution was continuously added dropwise to the first aqueous solution within 15 minutes. The color of the resulting mixed solution was dark violet.

The mixed solution was stirred at 25° C. for a further 30 minutes. Subsequently, the pH of the mixed solution was adjusted to the value of 2.2 by adding dilute aqueous sulfuric acid at 25° C. (the concentration of which was about 1 molar). All aforementioned working steps were performed under air.

Finally, the molecular oxygen present dissolved in the resulting acidic mixed solution was displaced by bubbling through a nitrogen stream at 25° C. (≥99.9 mol % of $N_2$; approx. 1500 ml/h) for 10 minutes. The final solution thus obtained was subsequently treated hydrothermally as described below.

b) Hydrothermal treatment of the aqueous final solution obtained in 1.a)

The shell of the reaction space in the autoclave was manufactured from Teflon and had the geometry of a hollow circular cylinder with a removable lid which was sealed with a Viton® O-ring. The wall thickness of the casing of the hollow Teflon cylinder was 7.5 mm, the internal diameter thereof was 60 mm, the base was 5.0 mm thick and the volume of the reaction space was 325 ml. The hollow Teflon cylinder was surrounded by a pressure-resistant casing with a lid which can be screwed on in a pressure-tight manner. The material from which it was manufactured was DIN 1.4301 stainless steel. Through the two lids, a Teflon-sheathed thermocouple was conducted into the reaction space (K type from TMH GmbH in D-63477 Maintal), with which the temperature in the reaction space was registered. The reaction interior was equipped with a Teflon-sheathed magnetic bar which could be set in rotating motion with the aid of a customary laboratory magnetic stirrer plate, in order to stir the reaction space. The heating was effected by means of four electrical heating cartridges (230 V, 400 W, from Heinz Stegmaier GmbH in D-78567 Fridingen), in two half-shell-shaped sleeves of aluminum (as the heating jacket), which surrounded the pressure-resistant stainless steel casing. To control the temperature program, a programmable process regulator (CAL 9500 P type from CAL Control Inc., Libertyville, Ill., 60048-3764, U.S.A.) was used. For temperature monitoring for this purpose, a further thermocouple was mounted in a fixed manner in the heating jacket. An additional thermocouple in the heating jacket served for safeguarding from excess temperature.

The aqueous final solution produced in 1.a) was introduced in its entirety, with a temperature of 25° C., into the ventilated reaction space of the autoclave. Subsequently, the autoclave including the reaction space was sealed pressure-tight. Thereafter, the solution stirred within the reaction space of the autoclave was heated at a heating rate of 5° C./min to a temperature of 175° C. and then held at this temperature (175° C.) while stirring over a further 24 h. Then the heating was ended and the contents of the reaction space were cooled in an essentially linear manner to 25° C. while continuing to stir within 7 h. The maximum operating pressure was about 1 MPa.

In the reaction space was an aqueous suspension. By filtration, the suspended solids were removed. The filtercake obtained was slurried in 120 ml of an aqueous oxalic acid solution at a temperature of 80° C. (oxalic acid concentration=0.4 mol/l solution (based on 25° C. and 101.3 kPa)) and the mixture was stirred while maintaining the 80° C. over a period of 1 h. Then the solids were filtered off again and washed with 200 ml of water, the temperature of which was 25° C. Subsequently, the solids were dried at a temperature of 80° C. in a forced-air drying cabinet for 10 h to give the precursor composition for the thermal treatment.

c) Thermal treatment (calcination) of the precursor composition obtained in 1.b)

The apparatus for thermal treatment comprised a quartz glass inner tube rotatable about its own longitudinal axis and an outer tube surrounding this inner tube.

The length of the outer tube was 52 cm. At a length of 36 cm the internal diameter of the outer tube was 4.8 cm, and at a length of 15 cm the internal diameter of the outer tube was 6.5 cm. The transition from internal diameter 4.8 cm to internal diameter 6.5 cm occurred over a length of 1 cm. At that end of the outer tube (the end E1) at which the outer tube had the greater cross section, the outer tube was closed with a quartz glass base. At the end opposite this end (the end E2), at which the outer tube had the smaller cross section, the outer tube was open.

The inner tube had a length of 49 cm. At a length of 37 cm, the internal diameter of the inner tube was 1.5 cm. For a subsequent length of 10 cm, the internal diameter of the shell of the inner tube was 3.4 cm (for this longitudinal section, the cross section of the inner tube was not circular but as shown in FIG. 1 of this document; this cross-sectional configuration was required by the action of a static stirrer) and, for a subsequent end length of 2 cm, the internal diameter of the inner tube was 1 cm.

The inner tube was open at both sides (ends). The glass thickness in both quartz glass tubes was 1.5 mm.

At the end E2 of the outer tube, the inner tube was conducted into the outer tube with its orifice having the smaller cross section leading, such that the longitudinal axes of both tubes coincided and a distance from the orifice of the smaller cross section of the inner tube to the glass base of the outer tube of 2 cm remained.

The dry precursor composition from 1.b), prior to the thermal treatment thereof, was triturated in a mortar and then introduced in its entirety into the section of the aforementioned inner tube which had a cross section according to FIG. 1, and fixed therein with quartz wool on both sides.

A glass-metal connection was used to secure the two glass tubes at the open side of the outer tube to a screw motor (from Faulhaber in D-71101 Schönach), which was able to rotate about its own axis at constant rotational speed. A Cr/Ni thermocouple which projected into the finely divided precursor composition controlled the temperature in the calcination material (in the precursor composition) using a Eurothermregler®.

At a length of 35 cm, with the bulging part thereof leading, the outer tube (and with it the inner tube) projected into a heatable muffle furnace from Heraeus.

From the side of the screw motor, it was possible to conduct a nitrogen stream (>99.95% by volume of $N_2$) into the inner tube, which flowed out of it again at the opposite end of the inner tube, with a flow rate controllable by means of a variable area flowmeter. Any gases released from the precursor composition during the calcining operation (the thermal treatment) and the nitrogen stream flowing out of the inner tube were removable via the outer tube.

At a nitrogen volume flow rate of 100 ml/min (this was supplied at a temperature of 25° C.) and a speed of the screw motor of 3 revolutions/min, the finely divided precursor composition (after it had been purged with the nitrogen stream for 30 min beforehand) was heated at a heating rate of 5° C./min to 500° C. Subsequently, this temperature (the 500° C.) was maintained while retaining the nitrogen stream for a further 120 min. Finally, the calcination material was cooled in an essentially linear manner to 25° C. within 10 h.

The particle sizes of the resulting comparative mixed oxide were in the range from 3 to 25 μm (longest dimension). The specific surface area SA was 66 m²/g. The stoichiometry of the comparative mixed oxide was $Mo_{12}V_4O_x$ (the respective mixed oxide stoichiometry was analyzed for this document by optical emission spectroscopy with inductively coupled plasma (ICP-OES) using an ICP Optima 3000 measuring instrument from Perkin Elmer, D-63110 Rodgau; for this purpose, 20 mg of the oxidic composition to be analyzed in each case were dissolved with 20 ml of a 2 molar aqueous sodium hydroxide solution (NaOH of the super pure purity grade from Merck, Darmstadt); the clear solution resulting in each case was subsequently diluted for the ICP-OES analysis with water in a weight ratio of 1 (solution) to 100 (water)).

d) Analysis of the catalytic performance of the finely divided comparative mixed oxide from 1.c) in long-term operation of a partial oxidation of acrolein to acrylic acid heterogeneously catalyzed by the comparative mixed oxide It is common knowledge that catalyst performance in the long-term operation of a heterogeneously catalyzed partial oxidation can be assessed, rather than by such a long-term operation, also by the corresponding performance in a less time-consuming temperature-programmed partial oxidation experiment (TPPE).

In such an experiment, a catalyst sample present in a reactor is exposed to a constant flow of a reaction gas mixture (constant flow rate, constant composition of the reaction gas mixture), and the temperature of the catalyst sample (of the finely divided active composition sample) is simultaneously varied in a controlled manner with time. The products and reactants leaving the reactor as a function of the temperature of the catalyst sample are observed. The proportions by volume thereof in the product gas mixture can be used to obtain, as a function of the respective temperature of the catalyst sample, characteristic parameters such as reactant conversion, selectivity of target product formation and yield of target product (based in each case on a single pass of the reaction gas mixture through the catalyst bed), which enable statements about the catalyst performance. By repeatedly running through the temperature program up to the region of elevated temperatures, which already cause marked total oxidation, the catalyst (the active composition) is deliberately exposed to elevated thermal stress over limited time periods, as a result of which the evolution of performance thereof over multiple runs through the temperature program enables an assessment of the long-term characteristics thereof in normal partial oxidation operation (cf. also WO 2005/047226 A1, "Long-term operation of a heterogeneously catalyzed gas phase partial oxidation of acrolein to acrylic acid").

In the TPPEs of this document, the reactor used was a hollow quartz glass cylinder which had been bent to a U-tube and introduced into a forced-air oven. The oven was electrically heatable and consisted of an aluminum housing in which there was a circular cylindrical ceramic sleeve open at the top and bottom, around which was wound heating wire, and in the interior of which the U-tube was positioned. It was possible to implement either variable heating rates or temperatures constant over time. To prevent the formation of a temperature gradient in the oven, an electrically operated propeller was mounted at the base thereof (below the ceramic sleeve), which brought about constant air circulation in the oven. For the purposes of cooling the reactor, cold gas could be fed directly into the oven interior. In addition, a cooling coil was introduced into the aluminum casing of the oven, through which cooling water could be conducted (a more detailed description of the forced-air oven/reactor construction can be found in S. Endres, Thesis, TU Darmstadt, 2009 and in J. Kunert, Thesis, TU Darmstadt 2003). The internal diameter of the quartz glass reactor tube was 0.4 cm. The wall thickness of the quartz glass was 1 mm. The two legs of the U-tube each had a length of 14 cm and were directed upward. The distance between the two legs was 3.3 cm.

For the performance of a TPPE, 50 mg in each case of the finely divided active composition to be analyzed were fixed between two glass wool plugs in the interior of the left-hand tube leg of the U-tube reactor (in the lower third of the tube leg length). For regulation of the temperature of the catalyst bed present in the reactor, a thermocouple was positioned in the middle thereof (K type, from TMH GmbH, in D-63477 Maintal).

The gas (mixture) to be supplied in each case, in the course of a temperature-programmed partial oxidation experiment (TPPE), was supplied to the orifice of the neck of the right-hand leg of the U-tube reactor. The feed temperature was, unless explicitly stated otherwise, 170° C. throughout. The volume flow rate of the gas (mixture) to be supplied in each case in all experiments was constant at 20 ml/min over the total duration of the experiment. The temperature of the catalyst sample present in the reactor was varied within the range between 100° C. and 480° C.

In order to put the finely divided mixed oxide to be subjected to the temperature-programmed partial oxidation experiment into a comparable starting state in each case (cf. WO 2005/047226 A1), it was first of all subjected in each case to a regenerative oxidative pretreatment while present in the reactor (referred to hereinafter as preoxidation).

For this purpose, a regeneration gas mixture (20 ml/min) was supplied (the feed temperature was likewise 170° C.), which consisted of 90% by volume of He and 10% by volume of molecular oxygen. The temperature of the finely divided mixed oxide sample was increased at a rate of 20° C./min from 25° C. to 400° C. This temperature was subsequently maintained for 60 min, as was the regeneration gas mixture stream. Then, under a gas stream (20 ml/min) consisting only of He (feed temperature=100° C.), the mixed oxide sample was cooled in an essentially linear manner to a temperature of 100° C. within 30 min.

While retaining the temperature of 100° C., this was followed by purging with the actual reaction gas mixture stream (20 ml/min), the feed temperature of which was likewise 100° C., during a ten minute run-in phase. In the case of the comparative mixed oxide $Mo_{12}V_4O_x$, in the case of the present comparative example 1.d), this had the following composition:
5% by vol. of acrolein,
10% by vol. of molecular oxygen, and
85% by vol. of helium.

The run-in phase was then followed by the actual TPPE.

For this purpose, while retaining the reaction gas mixture stream (20 ml/min, now feed temperature=170° C.), the temperature of the mixed oxide sample was heated at a heating rate of 10° C./min from 100° C. to 480° C. Then cooling was effected in an essentially linear manner to 400° C. under a pure He gas stream (inert gas stream) within 15 min (feed temperature=170° C.). This temperature was maintained for a period of 30 min and, during this period, regeneration was effected with the regeneration gas stream consisting of 90% by volume of He and 10% by volume of molecular oxygen (feed temperature=170° C.). Then the mixed oxide sample was cooled in an essentially linear manner to a temperature of 100° C. under a gas stream consisting solely of He (feed temperature=100° C.) within 30 min. This step completed the first TP partial oxidation cycle conducted after the preoxidation (including run-in phase).

There followed two further, identically executed TP partial oxidation cycles (including a respective run-in phase).

The product gas mixture was analyzed online with the aid of a mass spectrometer, to which the product gas mixture was supplied.

The mass spectrometer was a GAM 400 quadrupole mass spectrometer from InProcess Instruments in D-28201 Bremen. It had an intake system (quartz glass capillary) heatable to 200° C. and a cross beam ion source for electron impact ionization with ionization energy 70 eV and an SEM detector.

The temperature signal measured by means of the thermocouple present in the catalyst bed, and the proportions by volume of the product gas mixture, were recorded synchronously. In the assignment of "product gas mixture" and "temperature of the catalyst bed" it was taken into account that the conduction distance between catalyst bed and mass spectrometer, and within the mass spectrometer, for the product gas mixture caused a time delay (further details of experimental setup can be found in S. Endres, Thesis, TU Darmstadt, 2009).

Figure 2:
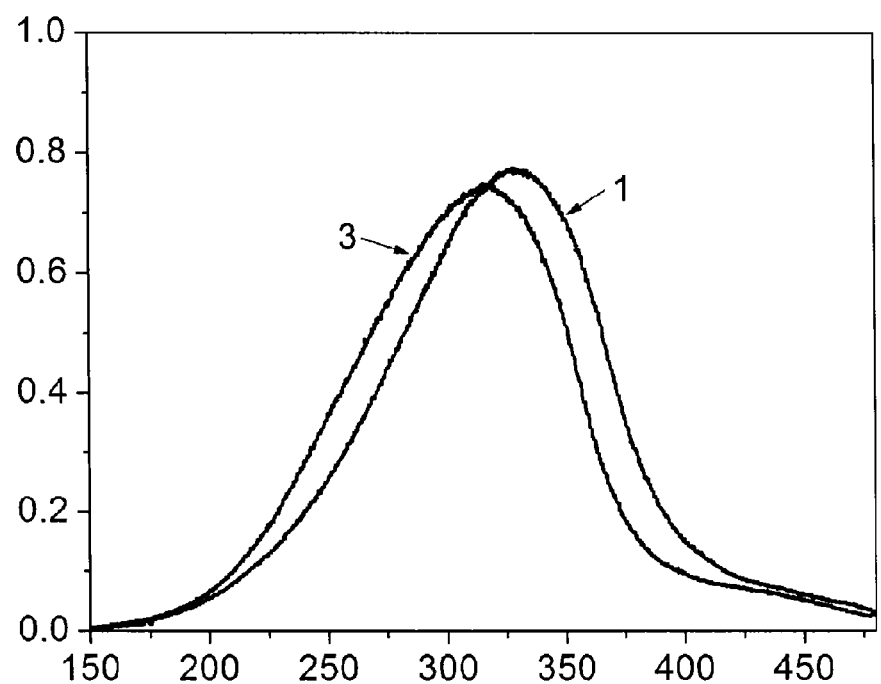
FIG. 2 shows a plot of the yield $Y^{AA}$ of acrylic acid as a function of the respective catalyst bed temperature both for the first (reference numeral 1 in FIG. 2) and the third (reference numeral 3 in FIG. 2) TP partial oxidation cycle.

In the first two TP partial oxidation cycles, in the case of the comparative mixed oxide $Mo_{12}V_4O_x$, the maximum yield $Y^{AA}$ of acrylic acid was attained at a catalyst bed temperature of 330° C. The value thereof was 77 mol %. As early as in the third TP partial oxidation cycle, the maximum yield $Y^{AA}$ of acrylic acid fell to 74 mol % and was at a catalyst bed temperature of only 320° C. These two decreases show that catalyst performance in long-term operation is not very stable in comparative terms. FIG. 2 of this document shows the plot of the yield $Y^{AA}$ of acrylic acid which results in each case as a function of the respective catalyst bed temperature both for the first (reference numeral 1 in FIG. 2) and the third (reference numeral 3 in FIG. 2) TP partial oxidation cycle. The abscissa of FIG. 2 shows the temperature of the catalyst bed in ° C., and the ordinate shows the yield $Y^{AA}$ in mol %/100.

2. Hydrothermal preparation of an inventive multimetal oxide of the stoichiometry $Mo_{12}V_3W_{2.25}O_x$ and analysis of the performance thereof in long-term operation of a partial oxidation of acrolein to acrylic acid heterogeneously catalyzed thereby a) Preparation of the aqueous mixture for hydrothermal treatment First 10 g (=56.6 mmol of Mo) of ammonium heptamolybdate tetrahydrate and then 2.9 g (=10.6 mmol of W) of ammonium metatungstate hydrate $[(NH_4)_6H_2W_{12}O_{41}\cdot18H_2O]$ were dissolved at 25° C. in 120 ml of water. After the resulting yellow solution had been stirred at 25° C. for a further 30 minutes, it formed a first aqueous solution.

By dissolving 3.69 g (=14.2 mmol of V) of a vanadyl sulfate hydrate in 120 ml of water at 25° C., a second aqueous solution was prepared. While constantly stirring the first aqueous solution, with maintenance of the 25° C., the second aqueous solution was continuously added dropwise to the first aqueous solution within 15 minutes. The color of the resulting aqueous solution was violet. Over 30 further minutes, it was stirred at 25° C. Subsequently, the pH of the mixed solution was adjusted to the value of 2.2 by adding dilute aqueous sulfuric acid (the concentration of which was about 1 molar).

All aforementioned working steps were conducted under air. Finally, the molecular oxygen present dissolved in the resulting acidic mixed solution was displaced by bubbling a nitrogen stream at 25° C. through it for 10 minutes (≥99.9 mol % of $N_2$; approx. 1500 ml/h).

The aqueous final solution thus obtained was subsequently hydrothermally treated as described below.

b) Hydrothermal treatment of the aqueous final solution obtained in 2.a)

The aqueous solution obtained in 2.a) was treated hydrothermally as described for the aqueous final solution obtained in 1.a). The suspended solids were removed by filtration from the resulting aqueous suspension, in a manner corresponding to that described in 1.b), washed with aqueous oxalic acid, then washed with water, and finally dried in a forced-air drying cabinet to give the precursor composition for thermal treatment.

c) Thermal treatment (calcination) of the precursor composition obtained in 2.b)

The thermal treatment of the precursor composition obtained in 2.b) was effected like the thermal treatment (calcination) of the precursor composition obtained in 1.b) in 1.c).

The particle sizes of the resulting multimetal oxide were in the range of 3 to 25 μm (longest dimension). The specific surface area SA was 36 m²/g (without conducting the washing with the aqueous oxalic acid/water in 2.b), SA was 35 m²/g). The stoichiometry of the multimetal oxide prepared in accordance with the invention was $Mo_{12}V_3W_{2.25}O_x$.

Figure 3:
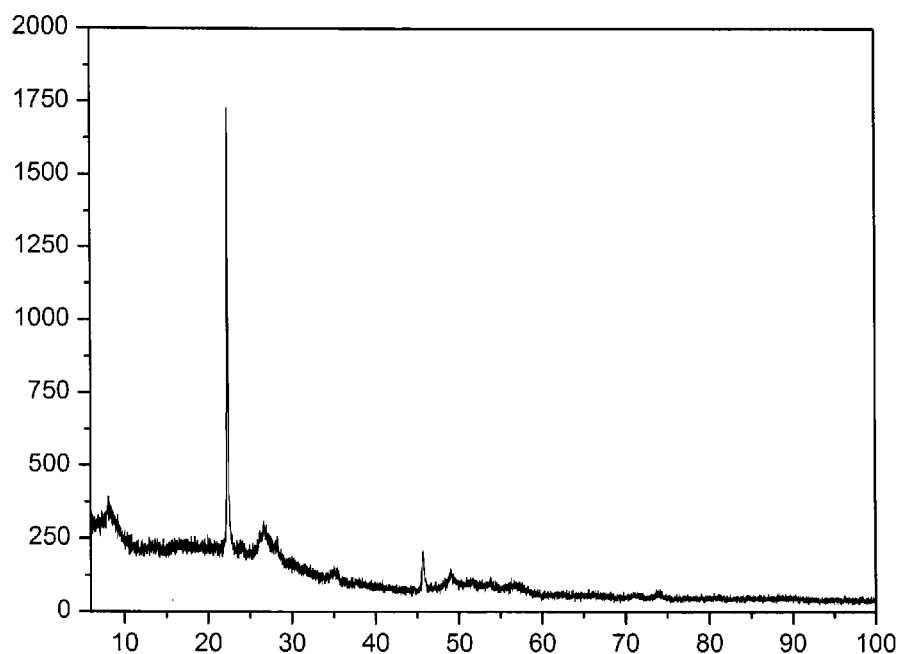
FIG. 3 shows an X-ray diffractogram of a multimetal oxide prepared according to one embodiment of the invention.
Figure 4:
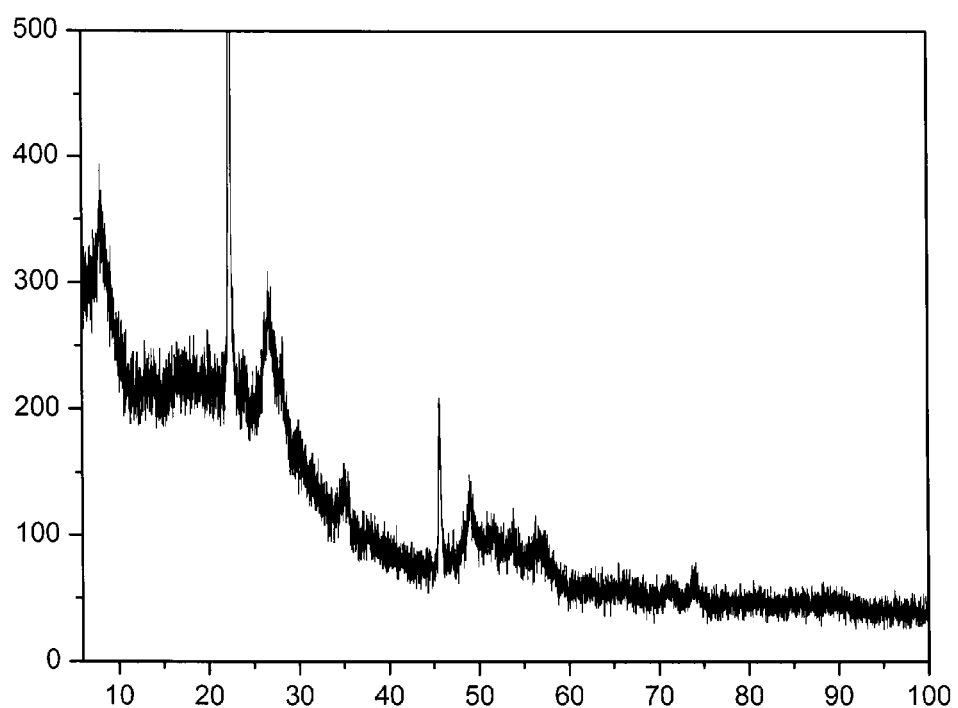
FIG. 4 shows an X-ray diffractogram of a multimetal oxide prepared according to one embodiment of the invention with a different scale from FIG. 3.

The X-ray diffractogram thereof is shown by FIGS. 3 and 4 of this document with a different scale for the absolute intensity. The abscissa shows the diffraction angle on the 2Θ scale [degrees]. The absolute intensity is plotted on the ordinate. On the basis of the presence of individual defined reflections, the structure is not X-ray-amorphous. A crystalline assignment is likewise not possible. The multimetal oxide powder can thus be described as semicrystalline.

SEM images (1000-fold magnification) of the multimetal oxide conducted on a DSM 962 scanning electron microscope from Carl Zeiss in D-73447 Oberkochen (the instrument had, for surface imaging, both an SE (secondary electrons) and a BSE ((back-scattered electrons) detector, and an EDX detector for elemental analysis) showed a sponge-like structure (irregularly roughened surface peppered with crystals). The surface consisted of rod-shaped crystals which had a length of approx. 1 μm.

d) analysis of the catalytic performance of the finely divided inventive multimetal oxide from 2.c) in long-term operation of a partial oxidation of acrolein to acrylic acid heterogeneously catalyzed by the inventive multimetal oxide For the purpose of assessing the catalyst performance in long-term operation of a correspondingly catalyzed partial oxidation of acrolein to acrylic acid, the TPPE comprising 3 TP partial oxidation cycles from 1.d) was repeated using the multimetal oxide from 2.c) as the catalytic active composition.

In the first partial oxidation cycle, the maximum yield $Y^{AA}$ of acrylic acid was attained at a catalyst bed temperature of 322° C. The value thereof was 79 mol %. In the two subsequent cycles, the maximum yield $Y^{AA}$ rose to 81 mol % and was at a catalyst bed temperature of 325° C. This stable TPPE behavior indicates marked stability of catalyst performance in long-term operation. Activity and selectivity of acrylic acid formation actually experience a small increase over the three TP partial oxidation cycles (without conducting the washing with the aqueous oxalic acid/water, the maximum yield $Y^{AA}$ in the third cycle was 73 mol %; the corresponding catalyst bed temperature was 350° C.; the catalyst performance was stable over all three cycles).

3. Noninventive preparation of a comparative multimetal oxide of the stoichiometry $Mo_{12}V_3W_{2.25}O_x$ according to a prior art process and analysis of the performance thereof in the long-term operation of a partial oxidation of acrolein to acrylic acid heterogeneously catalyzed thereby.

a) Preparation of an aqueous starting solution

In a glass round-bottom flask which had a capacity of 2 l, 41.998 g (=237.8 mmol of Mo) of ammonium molybdate tetrahydrate, 6.956 g (=59.5 mol of V) of ammonium metavanadate ($NH_4VO_3$) and 11.047 g (=44.6 mmol of W) of ammonium metatungstate hydrate were stirred in the sequence mentioned into a 1.5 l initial charge of water at a temperature of 25° C. By adding 60% by weight aqueous nitric acid, the pH of the aqueous mixture was adjusted to a value of 5. This was followed by stirring under reflux for another 90 minutes and then cooling to 25° C. The result was a clear yellow/orange aqueous solution.

b) Spray-drying of the aqueous solution obtained in 3.a)

The spray drying system used is described in J. Kunert, Thesis, TU Darmstadt 2003.

The aqueous solution to be spray-dried was initially charged at a temperature of 25° C. in an unstirred reservoir vessel. An HPLC pump (P700 type, from LATEK Labortechnik GmbH, D-69214 Eppelheim) was used to convey the aqueous solution at a volume flow rate of 12 ml/min into the two-phase nozzle of the spray tower. In the nozzle, the solution was atomized by a compressed air stream (607.8 kPa) and entrained by a hot (275° C.) dry air stream which was produced by a hot air blower (from Leister Process Technologies, CH-6056 Kaegiswil, Vulcan "E" type, 65 dB (A), static pressure 0.4 kPa, power: 9.9 to 13.3 kW), and dried to give a yellow pulverulent solid which was deposited in a cyclone. The nozzle diameter of the two-phase nozzle was 0.7 mm. The exit temperature from the drying tower was 90° C.

c) Thermal treatment (calcination) of the spray powder obtained in 3.b)

The thermal treatment of the spray powder obtained in 3.b) was effected as described in 1.c) for the precursor composition produced in 1.b).

However, the temperature program was configured as follows. First of all, heating was effected at a heating rate of 2° C./min to 325° C. This temperature was then maintained over 4 h. Thereafter, the temperature was increased at a heating rate of 2° C./min to 400° C. and this temperature was maintained over 10 min. Finally, the calcination material was cooled to 25° C. in an essentially linear manner within 10 h.

The particle sizes of the resulting comparative multimetal oxide were ≤13 μm (longest dimension). The specific surface area SA was 4 m²/g. The stoichiometry of the comparative multimetal oxide was $Mo_{12}V_3W_{2.25}O_x$.

Figure 5:
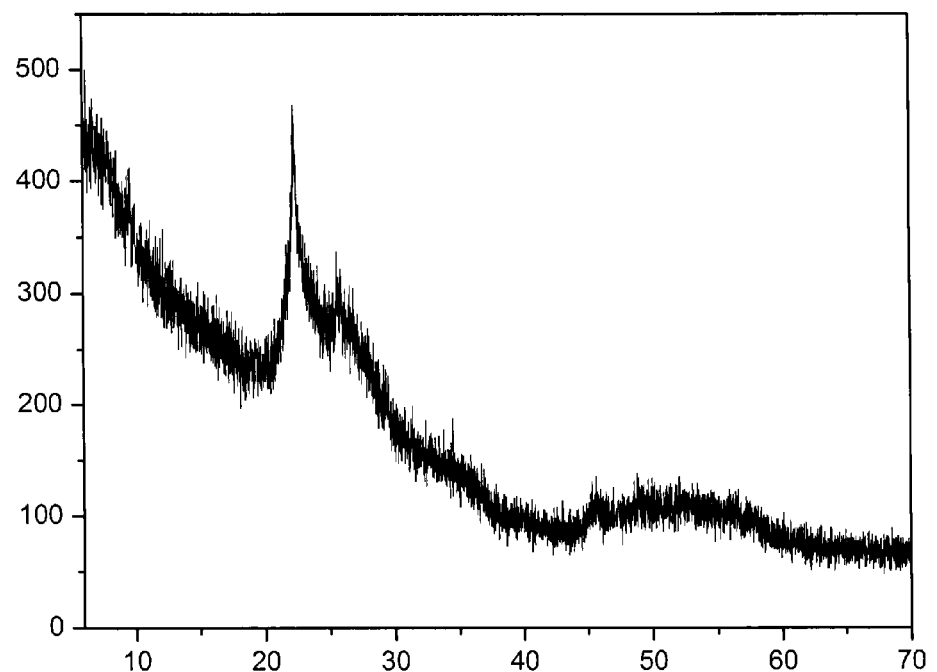
FIG. 5 shows an X-ray diffractogram of a comparative multimetal oxide.

The X-ray diffractogram thereof is shown by FIG. 5 of this document. The abscissa shows the diffraction angle on the 2Θ scale [degrees]. The absolute intensity is plotted on the ordinate. On the basis of the absence of defined reflections, the multimetal oxide powder can be regarded as X-ray-amorphous.

SEM images of the multimetal oxide showed spherical particles with a smooth surface. Such formation of hollow spheres is a known phenomenon for spray-drying operations.

d) Analysis of the catalytic performance of the finely divided noninventive multimetal oxide from 3.c) in the long-term operation of a partial oxidation of acrolein to acrylic acid heterogeneously catalyzed by this comparative multimetal oxide For the purpose of assessing catalyst performance in the long-term operation of a correspondingly catalyzed partial oxidation of acrolein to acrylic acid, the TPPE comprising three TP partial oxidation cycles from 1.d) was repeated using the comparative multimetal oxide from 3.c) as the catalytic active composition.

Over the three TP partial oxidation cycles, no decrease in the maximum yield $Y^{AA}$ of acrylic acid was observed. In the third TP partial oxidation cycle, the maximum yield $Y^{AA}$ was at a catalyst bed temperature of 442° C. and was 49 mol %.

4. Noninventive preparation of a comparative multimetal oxide of the stoichiometry $Mo_{12}V_3W_{2.25}O_x$ and analysis of the performance thereof in the long-term operation of a partial oxidation of acrolein to acrylic acid heterogeneously catalyzed thereby a) The preparation of the aqueous final solution from 2.a) was repeated.

b) The aqueous solution obtained in 4.a) was spray-dried.
The spray drying was effected like the spray drying of the aqueous solution obtained in 3.a) in 3.b).

c) The spray powder obtained in 4.b) was calcined. The thermal treatment (the calcination) was effected like the thermal treatment of the precursor composition obtained in 2.b) in 2.c). The resulting finely divided comparative multimetal oxide had the stoichiometry $Mo_{12}V_3W_{2.25}O_x$. The specific surface area SA thereof was 5.8 m²/g.

d) The analysis of the catalytic performance of the finely divided comparative multimetal oxide from 4.c) was effected as in 2.d) for the finely divided inventive multimetal oxide from 2.c).

Over the three TP partial oxidation cycles, no decrease in the maximum yield $Y^{AA}$ of acrylic acid was observed. In the third TP partial oxidation cycle, the maximum yield $Y^{AA}$ was at a catalyst bed temperature of 400° C. and was 40 mol %.

5. Inventive preparation of a multimetal oxide of the stoichiometry $Mo_{12}V_3W_{2.25}O_x$ by inventive hydrothermal aftertreatment of the comparative multimetal oxide from 3.c) and analysis of the performance thereof in the Long-Term operation of a partial oxidation of acrolein to acrylic acid heterogeneously catalyzed thereby 10 g of the pulverulent comparative multimetal oxide from 3.c) were suspended in 150 ml of water, and the resulting aqueous suspension was introduced into the reaction space of the autoclave from 1.b) and treated hydrothermally as described in 1.b).

After cooling to 25° C., an aqueous suspension was taken from the reaction space and the solids suspended therein were removed by means of centrifuging (a Beckmann J2/21 centrifuge was used; JA 14 rotor, 5000 rpm, 10750 g, 10 min).

The solid sediment removed was dried in a forced-air drying cabinet at 110° C. for 120 min and subsequent triturated in a mortar.

Stoichiometry of the resulting mixed oxide powder 5 was $Mo_{12}V_3W_{2.25}O_x$ within measurement accuracy. The specific surface area SA thereof was 138 m²/g.

Figure 6:
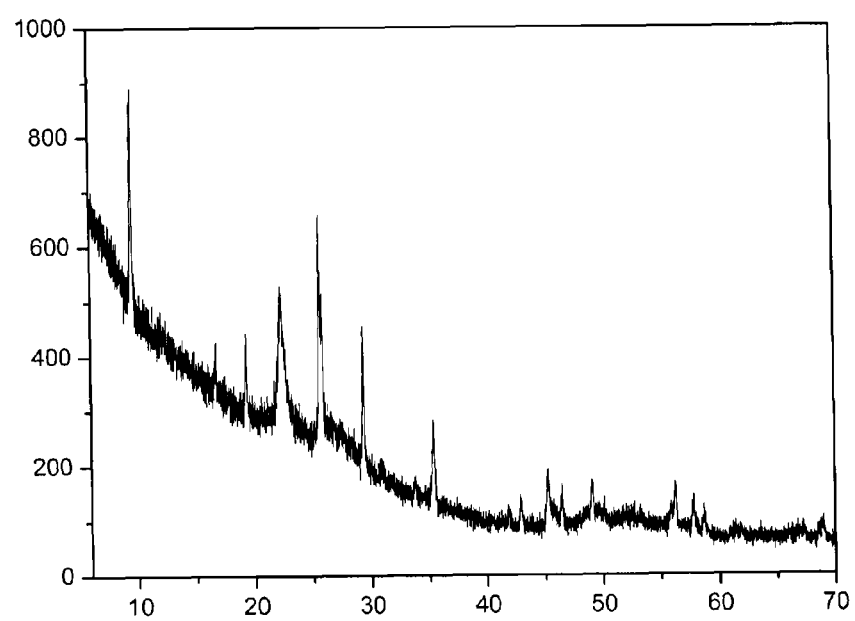
FIG. 6 shows an X-ray diffractogram of a multimetal oxide prepared according to one embodiment of the invention.

The corresponding X-ray diffractogram is shown in FIG. 6 of this document. The abscissa shows the diffraction angle on the 2Θ scale [degrees]. The absolute intensity is plotted on the ordinate. There are several defined reflections with low intensity. Overall, the specimen is merely semicrystalline.

SEM images of the multimetal oxide still showed spherical particles with reduced agglomeration compared to the comparative multimetal oxide from 3.c).

For the purpose of assessing the catalyst performance in long-term operation, the TPPE from 1.d) comprising 3 TP partial oxidation cycles was repeated using mixed oxide powder 5 as the active composition. Over the three TP partial oxidation cycles, no decrease in the maximum yield $Y^{AA}$ of acrylic acid was observed. In the third TP partial oxidation cycle, the maximum yield $Y^{AA}$ was at a catalyst bed temperature of 351.5° C. and was 63.5 mol %.

Figure 7:
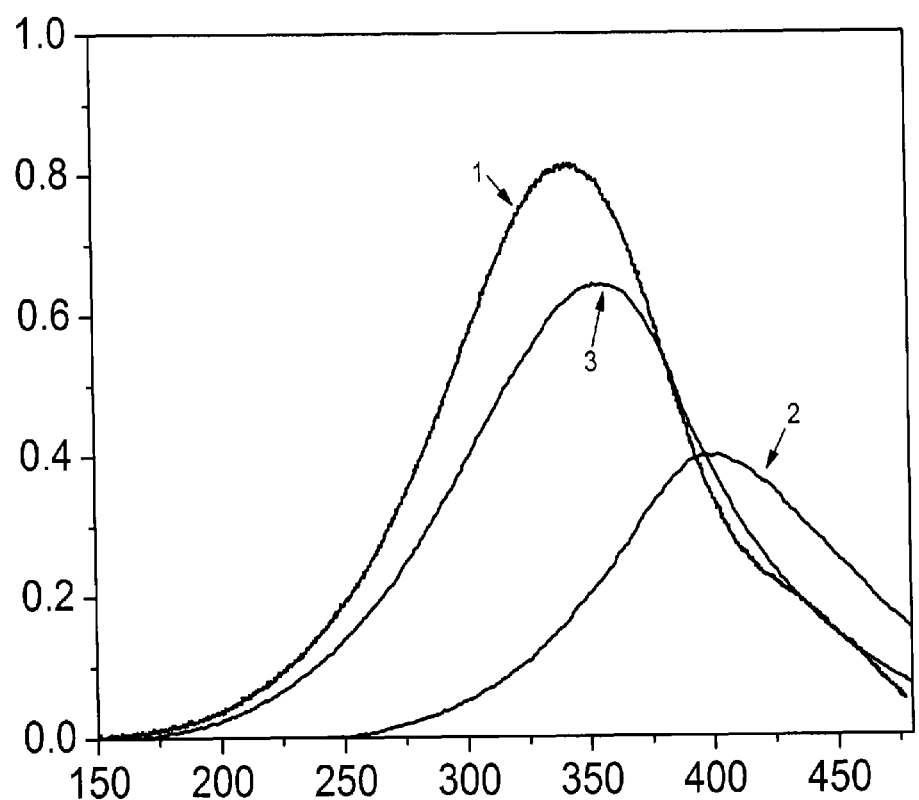
FIG. 7 shows a plot of the yield $Y^{AA}$ of acrylic acid as a function of the respective catalyst bed temperature in the third TP partial oxidation cycle, for the long-term operation both from 2.d) (reference numeral 1 in FIG. 7) and from 3.d) (reference numeral 2 in FIG. 7), and from 5. (reference numeral 3 in FIG. 7).

FIG. 7 of this document shows the plot of the yield $Y^{AA}$ of acrylic acid which results in each case as a function of the respective catalyst bed temperature in the third TP partial oxidation cycle, for the long-term operation both from 2.d) (reference numeral 1 in FIG. 7) and from 3.d) (reference numeral 2 in FIG. 7), and from 5. (reference numeral 3 in FIG. 7). The abscissa of FIG. 7 shows the temperature of the catalyst bed in ° C., and the ordinate shows the yield $Y^{AA}$ in mol %/100.

6. Analysis of the catalytic performance of the finely divided inventive multimetal oxide from 2.c) in the long-term operation of a partial oxidation of acrolein to acrylic acid heterogeneously catalyzed by this multimetal oxide The procedure was as in 2.d). The reaction gas mixture stream, however, had the following composition:
5% by vol. of acrolein,
10% by vol. of molecular oxygen,
7% by vol. of $H_2O$, and
78% by vol. of helium.

The maximum yield $Y^{AA}$ was essentially unchanged over the three TP partial oxidation cycles. It was 89 mol % in the third partial oxidation cycle and was attained at a catalyst bed temperature of 300° C.

7. Analysis of the catalytic performance of the finely divided inventive multimetal oxide from 5. in the long-term operation of a partial oxidation of acrolein to acrylic acid heterogeneously catalyzed by this multimetal oxide The procedure was as in 5. The reaction gas mixture stream, however, had the following composition:
5% by vol. of acrolein,
10% by vol. of molecular oxygen,
7% by vol. of $H_2O$, and
78% by vol. of helium.

The maximum yield $Y^{AA}$ was essentially unchanged over the three TP partial oxidation cycles. It was 74 mol % in the third partial oxidation cycle and was attained at a catalyst bed temperature of 324° C.

8. Analysis of the catalytic performance of the finely divided inventive multimetal oxide from 2.c) and of the finely divided noninventive multimetal oxide from 3.c) in the long-term operation of partial oxidations of methacrolein to methacrylic acid heterogeneously catalyzed by these multimetal oxides a) The procedure was as in 2.d) or as in 3.d). The reaction gas mixture stream, however, had the following composition:
5% by vol. of methacrolein,
10% by vol. of molecular oxygen, and
85% by vol. of helium.

The ratio of the maximum yields $Y^{MA}$ of methacrylic acid established in the third TP partial oxidation cycle in each case was $Y^{MA}(2.d):Y^{MA}(3.d)=2.2.$ In the case of use of the inventive multimetal oxide from 2.c), the maximum in the methacryclic acid yield in the third TP partial oxidation cycle was established at a catalyst bed temperature of 360° C.

In the case of use of the noninventive comparative multimetal oxide from 3.c), the maximum in the methacrylic acid yield in the third TP partial oxidation cycle was established at a catalyst bed temperature of 417° C.

b) The TPPE from 8.a) with the inventive multimetal oxide from 2.c) was repeated, except that the reaction gas mixture stream had the following composition:
5% by vol. of methacrolein,
10% by vol. of molecular oxygen,
7% by vol. of $H_2O$, and
78% by vol. of helium.

Compared to the maximum yield $Y^{MA}$ of methacrylic acid achieved in the third cycle of the TPPE from 8.a), the maximum yield of methacrylic acid in the third cycle of the TPPE in 8.b) was greater by a factor of 1.41. It was established at a catalyst bed temperature of 350° C.

9. Preparation of an eggshell catalyst EC1 with an inventive catalytically active multimetal oxide composition of the stoichiometry $mo_{12}v_{3.3}w_{3.24}O_x$ (in the details given below, any hydrate water present is not addressed explicitly)

In a glass 4-neck flask which had a capacity of 4 l and which was equipped with a stirrer apparatus, 87.2 g of ammonium heptamolybdate (=495.3 mmol of Mo, from H. C. Starck GmbH) were dissolved in 1.046 l of water, the temperature of which was 25° C., while maintaining the 25° C. Thereafter, 24.7 g of ammonium paratungstate (=95.4 mmol of W, from BASF SE) were added and the resulting aqueous mixture was stirred at 80° C. for 30 minutes. The resulting solution at 80° C. constituted solution I.

33.9 g of vanadyl sulfate (=127.2 mmol of V, from Fischer Scientific) were added to 1.046 l of water at a temperature of 80° C., and dissolved to give solution II while stirring and maintaining the 80° C.

While maintaining the 80° C., solution II was stirred into solution I. Then the mixture was cooled to 25° C. The pH of the resulting solution was adjusted to 2.0 by adding 1 molar sulfuric acid while stirring. Thereafter, the molecular oxygen dissolved in the solution was displaced by passing molecular nitrogen through (the $O_2$ content of the $N_2$ was <10 ppm by vol.) for 10 minutes.

Subsequently, the solution was introduced under air into the non-Teflon-lined stirred reaction space of an autoclave (constructed in-house by BASF SE). The reaction space had a capacity of 3.5 l and had a shell manufactured from Hastelloy C. A thermocouple projected into the reaction space for temperature monitoring. The air present in the gas phase of the filled autoclave was subsequently displaced with molecular nitrogen. For this purpose, three times in succession, the autoclave was filled with 5 bar nitrogen (the $O_2$ content of which was <20 ppm by vol.) and immediately decompressed again to ambient pressure each time. Thereafter, the autoclave was heated to 175° C. at a heating rate of 5° C./min while stirring (rotation rate: 500 rpm). This temperature was maintained while stirring for 24 hours. Then, while continuing to stir, cooling was effected to 25° C. in an essentially linear manner within 2.5 hours, and then purging was effected again, three times in succession with molecular nitrogen (<20 ppm by vol. of $O_2$). For this purpose, the pressure in the autoclave was brought to 5 bar in each case with the nitrogen and, on attainment of the 5 bar, released again immediately to ambient pressure (atmospheric pressure). Then the autoclave was opened and the aqueous suspension present was sucked out of the autoclave through a ceramic suction filter (from Witeg Labortechnik GmbH, D-97877 Wertheim, pore size 4), and the filtercake obtained was dried in a forced-air drying cabinet at 80° C. for 16 h. The dried filtercake was slurried in 1 l of a 0.4 molar (based on standard conditions) solution of oxalic acid in water at 70° C. by stirring, and then stirred at 70° C. for 1 h (rotation rate: 300 rpm). Then the mixture was filtered with suction again through a ceramic suction filter (from Witeg Labortechnik GmbH, D-97877 Wertheim, pore size 4). The resulting filtercake was washed three times with 100 ml each time of water at 25° C., and finally dried again at 80° C. in a forced-air drying cabinet for 16 h (to cover the demand for precursor composition, the preparation method described so far was reproduced 12 times).

The entire amount of precursor composition taken from the forced-air drying cabinet was subsequently ground in a ZM 200 mill from Retsch to give a fine powder, of which 50% of the powder particles passed through a sieve of mesh size 1 to 10 μm and in which the numerical proportion of particles having a longest dimension above 50 μm was less than 1% (a particle diameter distribution particularly suitable in accordance with the invention at this point is shown in FIG. 3 of DE 102007010422 A1).

The thermal treatment (calcination) of the finely divided precursor composition was effected in 180 g portions in a rotary sphere oven as shown in FIG. 1 of DE 10033121 A1. The rotary sphere oven consisted of a 1 l quartz glass round-bottom flask on a rotary evaporator. The round-bottom flask was in an oven. Over the entire calcination (including cooling), a gas stream of 50 l (STP)/h (the l (STP) relate here to 25° C. and 101.3 kPa) of molecular nitrogen (<10 ppm by vol. of $O_2$) was passed through the rotary tube. This was supplied to the rotary tube oven with a temperature of 25° C. During the calcination, the round-bottom flask rotated at a rotation rate of 7 rpm.

Over the course of the thermal treatment, the precursor composition present in the round-bottom flask was first of all heated from 25° C. in a linear manner to a material temperature (thermocouple-monitored) of 350° C. within 70 minutes. Subsequently, this material temperature was maintained for 1 hour. Thereafter, the material temperature was heated in an essentially linear manner to 450° C. within 20 min, and this temperature was maintained over 1 minute. Subsequently, the material temperature was increased to 500° C. in a linear manner within 20 minutes, and this temperature was maintained for 2 minutes. Thereafter, the rotary sphere oven contents were cooled in an essentially linear manner to 25° C. within 2.5 h.

The finely divided catalytically active multimetal oxide composition taken from the rotary sphere oven (the specific BET surface area of which was 30 m²/g) was subsequently used as in example S1 of EP 714700 A2 to coat 800 g of annular support bodies (external diameter 7 mm, length 3 mm, internal diameter 4 mm, C220 steatite from CeramTec with a surface roughness $R_z$ of 45 μm (grit layer; name: "7×3×4 Steatite ring porous coated")) (except that in contrast to the aforementioned example S1, the active composition content selected was approx. 20% by weight (based on the total weight of support body and active composition)). The total pore volume of a support body based on the volume of the mass of a support body was ≤1% by volume. Binder, as in example S1 of EP 714700 A2, was an aqueous solution of 75% by weight of water and 25% by weight of glycerol. The coating was effected in a rotating coating drum (internal diameter=25.5 cm; 36 rpm) which had been filled with the support bodies. About 70 ml of liquid binder was sprayed onto the support bodies using a nozzle (nozzle diameter=1 mm) within 40 minutes (the exact amount of binder in each case was such that no twin bodies were formed, but the entire amount of powder was taken up onto the surface of the support bodies without occurrence of powder agglomeration). At the same time, over the same period, 205 g of the catalytically active multimetal oxide composition powder were metered in continuously by means of a conveying screw outside the spray cone of the atomizer nozzle. During the coating, the powder supplied was taken up completely onto the surface of the support bodies. No agglomeration of the finely divided oxidic active composition was observed.

Subsequently, the coated rings were held at a temperature of 300° C. in a forced-air drying cabinet for 2 h (demoisturized). The eggshell catalysts EC1 taken from the forced-air drying cabinet had, based on the total mass thereof, an oxidic active composition content of 19% by weight.

The stoichiometry of the active composition shell of the eggshell catalyst EC1 was $Mo_{12}V_{3.3}W_{3.24}O_x$.

10. Preparation of an Eggshell Catalyst EC2 with an Inventive Catalytically Active Multimetal Oxide Composition of the Stoichiometry $Mo_{12}V_{3.2}W_{1.9}Cu_{0.4}O_x$ (In the Details Given Below, Any Hydrate Water Present is Not Addressed Explicitly))

The preparation of the annular eggshell catalyst EC2 was effected like the preparation of the eggshell catalyst EC1. However, the aqueous solution I comprised, rather than the 24.7 g of ammonium paratungstate, only 13.1 g of the same substance dissolved in the same amount of water as W source, and solution II comprised 28.3 g of vanadyl sulfate (from Fischer Scientific) and 12.6 g of copper(II) sulfate (=50.5 mmol of Cu, Sigma Aldrich) dissolved in 1.046 l of water.

The stoichiometry of the resulting finely divided active composition was $Mo_{12}V_{3.2}W_{1.9}Cu_{0.4}O_x$. The BET surface area SA thereof after calcination was 30 m²/g and, based on the total mass of the eggshell catalyst EC2, the oxidic active composition content was 18.8% by weight.

11. Preparation of a comparative eggshell catalyst CEC1 with a noninventive catalytically active multimetal oxide composition of the stoichiometry $Mo_{12}V_3W_{2.25}O_x$ 450.0 g of ammonium heptamolybdate tetrahydrate (Mo content=54.5% by weight) were dissolved in 5400 g of water at 90° C. within 5 minutes. Subsequently, while maintaining the 90° C., 82.0 g of ammonium metavanadate (V content=43.5% by weight) were added and the resulting solution was stirred at 90° C. for a further 40 minutes. Then 175.4 g of ammonium paratungstate heptahydrate (W content=71% by weight) were added and the resulting solution was stirred at 90° C. for a further 30 minutes.

The aqueous solution was subsequently spray-dried at an inlet temperature of 330° C. and an outlet temperature of 106° C. in an air stream within 1 h (spray tower from NIRO, spray head No. F0A1). During the spray drying, stirring of the as yet unsprayed proportion of the suspension was continued in each case while maintaining the 90° C.

The resulting spray powder, fully corresponding to the procedure with the spray powder in comparative example 1B of DE 102010023312 A1, was processed further to give annular comparative eggshell catalyst CEC1 (the annular support used and the coating method corresponded to those in "9." of this (the present) document). The highest material temperature in the calcination was 400° C.

The stoichiometry of the active composition was $Mo_{12}V_3W_{2.25}O_x$. The BET surface area SA thereof after calcination was 13.3 m²/g and, based on the total mass of the eggshell catalyst CEC1, the oxidic active composition content was 20% by weight.

12. Preparation of a comparative eggshell catalyst CEC2 with a noninventive catalytically active multimetal oxide composition of the stoichiometry $Mo_{12}V_3W_{1.2}Cu_{0.6}O_x$ The preparation was effected as described in comparative example 1B of DE 102010023312 A1. The aqueous solution of the elemental constituents was spray-dried and the resulting spray powder was processed further to give annular comparative eggshell catalysts CEC2 (the annular support used and the coating method corresponded to those in "9." of this (the present) document). The highest material temperature in the calcination was 400° C.

The stoichiometry of the active composition was $Mo_{12}V_3W_{1.2}Cu_{0.6}O_x$. The BET surface area SA thereof after calcination was 15 m²/g and, based on the total mass of the eggshell catalyst CEC1, the oxidic active composition content was 20% by weight.

13. Testing of eggshell catalysts EC1, EC2, CEC1 and CEC2 as catalysts for the heterogeneously catalyzed partial gas phase oxidation of acrolein to acrylic acid The eggshell catalysts were each tested in a reaction tube (V2A steel; external diameter 30 mm; wall thickness 2 mm; internal diameter 26 mm; length 465 cm) around which a salt bath flowed (mixture of 53% by weight of potassium nitrate, 40% by weight of sodium nitrite and 7% by weight of sodium nitrate), and which was charged from the top downward as follows:

Section 1: length 79 cm
  Empty tube;
Section 2: length 62 cm
  Preliminary bed of steatite rings of geometry 7 mm×3 mm×4 mm (external diameter×length×internal diameter; C220 Steatite from CeramTec);
Section 3: length 100 cm
  Fixed catalyst bed composed of a homogeneous mixture consisting of 15% by weight of steatite rings of geometry 7 mm×3 mm×4 mm (external diameter×length× internal diameter; C220 steatite from CeramTec) and 80% by weight of the respective eggshell catalyst;
Section 4: length 200 cm
  Fixed catalyst bed exclusively consisting of the eggshell catalyst also used in section 3 in each case;
Section 5: length 10 cm
  Subsequent bed of the same steatite rings as in section 2;
Section 6: length 14 cm
  Catalyst support made from V2A steel for accommodation of the fixed catalyst bed.

The reaction gas mixture had the following starting composition:
  acrolein 4.3% by vol.,
  propene 0.2% by vol.,
  propane 0.2% by vol.,
  acrylic acid 0.3% by vol.,
  $O_2$ 5.4% by vol.,
  $H_2O$ 7% by vol.,
  CO and $CO_2$ 0.4% by vol., and
  $N_2$ 82.2% by vol.

It flowed through the reaction tube from the top downward in each case.

The acrolein space velocity (as defined in DE 19927624 A1) on the fixed catalyst bed was set in each case to 75 l (STP)/l·h.

50 kg of stirred and externally electrically heated salt melt flowed around the length of the reaction tube (apart from the last 10 cm of the empty tube in section 1 and the last 3 cm of the tube in section 6) (the flow rate at the tube was 3 m/s).

The salt bath temperature ($T^B$, °C.) with which the salt bath was supplied was set in each case such that the conversion of acrolein ($C^A$, mol %), based on a single pass of the reaction gas mixture through the catalyst bed, was approx. 99.2 mol %. The inlet temperature of the reaction gas mixture (at the inlet into the reaction tube) was adjusted to the respective salt bath temperature.

Along the reaction tube, the salt bath temperature did not change as a result of heating (more heat was radiated from the salt bath than released from the reaction tube to the salt bath).

Table 1 below shows the results as a function of the eggshell catalyst used after 100 hours of operation in each case ($S^{AA}$=selectivity of acrylic acid formation):

TABLE 1

| Eggshell catalyst | $T^B$ (° C.) | $C^A$ (mol %) | $S^{AA}$ (mol %) |
|---|---|---|---|
| EC1 | 242.4 | 99.1 | 92.6 |
| EC2 | 251.0 | 99.2 | 97.0 |
| CEC1 | 293.6 | 99.3 | 91.8 |
| CEC2 | 270.0 | 99.3 | 97.0 |

The invention claimed is:

1. A process, comprising heterogeneously catalyzing a partial oxidation of (meth)acrolein to (meth)acrylic acid in the gas phase over a catalytically active multimetal oxide composition of formula (I):

$$Mo_{12}V_aX^1_bX^2_cX^3_dX^4_eX^5_fX^6_gO_n \qquad (I),$$

wherein:
  $X^1$ represents W, Nb, Ta, Cr, Ce, or a mixture thereof;
  $X^2$ represents Cu, Ni, Co, Fe, Mn, Zn, or a mixture thereof;
  $X^3$ represents Sb, Te, Bi, or a mixture thereof;
  $X^4$ represents H, one or more alkali metals, or a mixture thereof;
  $X^5$ represents one or more alkaline earth metals;
  $X^6$ represents Si, Al, Ti, Zr, or a mixture thereof;
  a represents 1 to 6;
  b represents 0.2 to 8;
  c represents 0 to 18;
  d represents 0 to 40;
  e represents 0 to 4;
  f represents 0 to 4;
  g represents 0 to 40;
  n represents a number determined by the valency and frequency of the elements in the formula (I) other than oxygen;
  at least 50 mol% of a total molar amount of elements $X^1$ present in the multimetal oxide composition of formula (I) is the element W;
  the multimetal oxide composition of formula (I) is prepared by hydrothermally treating a mixture of sources of elemental constituents in the presence of water in a pressure vessel, such that a newly forming solid is removed as a precursor composition which is converted to the catalytically active multimetal oxide composition of formula (I) by thermal treatment; and an aqueous mixture subjected to the hydrothermally treating at 25° C. and 103.1 kPa has a pH of ≥1 and ≤3.

2. The process according to claim 1, wherein the catalytically active multimetal oxide composition satisfies formula (II):

$$Mo_{12}V_aX^1_bX^2_cX^4_eX^5_fX^6_gO_n \quad (II),$$

wherein:
$X^1$ represents W, Nb, or a mixture thereof;
$X^2$ represents Cu, Ni, or a mixture thereof;
$X^4$ represents H;
$X^5$ represents Ca Sr, or a mixture thereof;
$X^6$ represents Si, Al, or a mixture thereof;
a represents 2 to 4;
b represents 0.2 to 3;
c represents 0.5 to 3;
e represents 0 to 2;
f represents 0 to 0.5;
g represents 0 to 8; and
n represents a number determined by the valency and frequency of the elements in the formula (II) other than oxygen.

3. The process according to claim 2, wherein at least 50 mol% of a total molar amount of elements $X^2$ present in the multimetal oxide composition of formula (II) is the element Cu.

4. The process according to claim 1, wherein the catalytically active multimetal oxide composition satisfies the formula (III):

$$Mo_{12}V_aW_bCu_cX^4_eX^5_fX^6_gO_n \quad (III),$$

wherein:
$X^4$ represents H, one or more alkali metals, or a mixture thereof;
$X^5$ represents one or more alkaline earth metals;
$X^6$ represents one or more selected from the group consisting of Si, Al, Ti and Zr;
a represents 2 to 4;
b represents 0.2 to 3;
c represents 0.5 to 2;
e represents 0 to 4;
f represents 0 to 4, with the proviso that a sum of e and f does not exceed 4;
g represents 0 to 40; and
n represents a number determined by the valency and frequency of the elements in the formula (III) other than oxygen.

5. The process according to claim 1, wherein the hydrothermally treating occurs at temperatures in the range of >100° C. to 600° C.

6. The process according to claim 1, wherein the hydrothermally treating occurs at a superatmospheric working pressure of ≤50 MPa.

7. The process according to claim 1, wherein, based on amounts of water and sources of the elemental constituents present in the pressure vessel during the hydrothermally treating, a proportion by weight of a total amount of the sources is 3 to 60% by weight.

8. The process according to claim 1, wherein at least one source of the vanadium of the formula (I) comprises vanadium in the +4 oxidation state.

9. The process according to claim 1, wherein removal of the solid newly forming in the hydrothermally treating comprises at least one mechanical removal of the solid and at least one washing operation on mechanically removed solid with at least one wash liquid selected from the group consisting of an organic acid, an inorganic acid and an aqueous solution thereof.

10. The process according to claim 1, wherein a temperature of hydrothermally treating is 350 to 650° C.

11. The process according to claim 1, wherein the catalytically active multimetal oxide composition is an active composition of an eggshell catalyst in which it has been applied to the surface of a support body.

12. The process according to claim 1, wherein a specific surface area of the active multimetal oxide composition is ≥15 m²/g.

13. The process according to claim 1, wherein b is 0.2.

14. The process according to claim 1, comprising heterogeneously catalyzing a partial oxidation of acrolein to acrylic acid.

* * * * *